United States Patent
Huang et al.

(10) Patent No.: US 11,988,663 B2
(45) Date of Patent: *May 21, 2024

(54) COMPOSITIONS AND METHODS FOR THE DETECTION AND MOLECULAR PROFILING OF MEMBRANE BOUND VESICLES

(71) Applicant: THE UNIVERSITY OF MEMPHIS RESEARCH FOUNDATION, Memphis, TN (US)

(72) Inventors: Xiaohua Huang, Memphis, TN (US); Thang Ba Hoang, Memphis, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 516 days.

This patent is subject to a terminal disclaimer.

(21) Appl. No.: 16/719,278

(22) Filed: Dec. 18, 2019

(65) Prior Publication Data

US 2020/0191778 A1    Jun. 18, 2020

Related U.S. Application Data

(60) Provisional application No. 62/781,297, filed on Dec. 18, 2018.

(51) Int. Cl.
*G01N 33/533* (2006.01)
*G01N 21/64* (2006.01)
*G01N 33/52* (2006.01)

(52) U.S. Cl.
CPC ....... *G01N 33/533* (2013.01); *G01N 21/6428* (2013.01); *G01N 33/52* (2013.01); *G01N 2021/6439* (2013.01)

(58) Field of Classification Search
CPC .. G01N 33/588; G01N 33/52; G01N 21/6428; G01N 33/582; G01N 33/533;
(Continued)

(56) References Cited

U.S. PATENT DOCUMENTS 5,837,832 A    11/1998 Chee et al.
6,436,665 B1    8/2002 Kuimelis
(Continued)

FOREIGN PATENT DOCUMENTS

WO    2013126774 A2    8/2013
WO    2015112382 A1    7/2015
(Continued)

OTHER PUBLICATIONS

Jain et al. Evaluation of quantum dot immunofluorescence and a digital CMOS imaging system as an alternative to conventional organic fluorescence dyes and laser scanning for quantifying protein microarrays. Proteomics 2016, vol. 16, No. 8, pp. 1271-1279. (Year: 2016).*

(Continued)

*Primary Examiner* — Shafiqul Haq
(74) *Attorney, Agent, or Firm* — Melissa Hunter-Ensor; Maximilian Benz; Greenberg Traurig, LLP

(57) ABSTRACT

The present disclosure features compositions and methods related to the detection and molecular profiling of extracellular vesicles using fluorescent probes. These compositions and methods leverage the unique optoelectrical properties of quantum dots and fluorescently labeled nanoparticles, which allows reliable, real-time detection of extracellular vesicles and vesicle surface bound or lumenal molecules.

8 Claims, 18 Drawing Sheets

(58) Field of Classification Search
CPC ........... G01N 21/6458; G01N 21/6452; G01N 2021/6439; G01N 2021/6417
See application file for complete search history.

(56) References Cited

U.S. PATENT DOCUMENTS

| | | |
|---|---|---|
| 2006/0119853 A1 | 6/2006 | Baumberg et al. |
| 2010/0253940 A1 | 10/2010 | Xia et al. |
| 2011/0128536 A1 | 6/2011 | Bond et al. |
| 2011/0168954 A1 | 7/2011 | Stevens |
| 2013/0004967 A1 | 1/2013 | Halverson et al. |
| 2013/0156706 A1 | 6/2013 | Bettinger et al. |
| 2013/0172207 A1 | 7/2013 | Dai et al. |
| 2014/0302492 A1 | 10/2014 | Blackburn et al. |
| 2015/0037818 A1 | 2/2015 | Huang et al. |
| 2015/0051459 A1 | 2/2015 | Van Duyne et al. |
| 2016/0033486 A1 | 2/2016 | Itonaga et al. |
| 2016/0146799 A1 | 5/2016 | Robinson et al. |
| 2016/0320390 A1 | 11/2016 | Newman et al. |
| 2018/0340945 A1* | 11/2018 | Mitsuhashi ........ G01N 33/6896 |
| 2021/0190774 A1* | 6/2021 | Huang ............. G01N 33/54346 |

FOREIGN PATENT DOCUMENTS

| | | |
|---|---|---|
| WO | 2017066390 A1 | 4/2017 |
| WO | 2017103245 A1 | 6/2017 |

OTHER PUBLICATIONS

Welch et al. Orientation and characterization of immobilized antibodies for improved immunoassays. Biointerphases 2017, vol. 12, No. 2, pp. 1-12. (Year: 2017).*

Salih et al. An immunoassay for urinary extracellular vesicles. Am. J. Renal Physiol. 2015, vol. 310, pp. F796-F801 (Year: 2015).*

Weigel et al. Dark Field Microspectroscopy with Single Molecule Fluorescence sensitivity. ACS Photonics, 2014, vol. 1, pp. 848-856. (Year: 2014).*

Ge, Hui, "UPA, a universal protein array system for quantitative detection of protein—protein, protein—DNA, protein—RNA and protein—ligand interactions," Nucleic Acids Research, Jan. 2000; vol. 28, Iss. 2, p. e3.

Lockhart, et al. "Expression monitoring by hybridization to high-density oligonucleotide arrays," Nature Biotechnology, Dec. 1996, vol. 14, Iss. 13, pp. 1675-1680.

MacBeath et al., "Printing Proteins as Microarrays for High-Throughput Function Determination," Science, 2000; vol. 289, Iss. 5485, pp. 1760-1763.

Schena et al., "Parallel human genome analysis: microarray-based expression monitoring of 1000 genes," Proceedings of the National Academy of Sciences, Oct. 1996; vol. 93, Iss. 20, pp. 10614-10619.

Zhu et al., "Analysis of yeast protein kinases using protein chips," Nature Genetics, Nov. 2000; vol. 26, Iss. 3, pp. 283-289.

Lai et al., "Dynamic Biodistribution of Extracellular Vesicles In Vivo Using a Multimodal Imaging Reporter," ACS Nano, Jan. 9, 2014, vol. 8, No. 1, pp. 483-494 (19 pages).

International Search Report and Written Opinion in corresponding PCT Patent Application No. PCT/US2019/067183, dated Mar. 16, 2020 (16 pages).

Bhana et al., "Capture and detection of cancer cells in whole blood with magnetic-optical nanoovals," Nanomedicine, 2014, vol. 9, No. 5, pp. 593-606.

Bhana et al., "Photosensitizer-loaded Gold Nanorods for Near Infrared Photodynamic and Photothermal Cancer Therapy," Journal of Colloid and Interface Science, 2016, vol. 469, pp. 8-16.

Campion et al., "Surface-enhanced Raman scattering," Chemical Society Reviews, 1998, vol. 27, No. 4, pp. 241-250.

Grasso et al., "Molecular screening of cancer-derived exosomes by surface plasmon resonance spectroscopy," Analytical and Bioanalytical Chemistry, 2015, vol. 407, pp. 5425-5432.

Hao et al., "Electromagnetic fields around silver nanoparticles and dimers," Journal of Chemical Physics, Jan. 1, 2004, vol. 120, No. 1, pp. 357-366.

Huang et al., "Cancer Cell Imaging and Photothermal Therapy in the Near-Infrared Region by Using Gold Nanorods," Journal of the American Chemical Society, 2006, vol. 128, No. 6, pp. 2115-2120.

Im et al., "Label-free detection and molecular profiling of exosomes with a nano-plasmonic sensor," Nature Biotechnology, May 2014, vol. 32, No. 5, pp. 490-495.

Kneipp et al., "Surface-enhanced Raman scattering and biophysics," Journal of Physics: Condensed Matter, 2002, vol. 14, pp. R597-R624.

Lee et al., "3D plasmonic nanobowl platform for the study of exosomes in solution," Nanoscale, 2015, vol. 7, pp. 9290-9297.

Liang et al., "Nanoplasmonic quantification of tumour-derived extracellular vesicles in plasma microsamples for diagnosis and treatment monitoring," Nature Biomedical Engineering, 2017, vol. 1, Article No. 0021, pp. 1-11.

Park et al., "Exosome Classification by Pattern Analysis of Surface-Enhanced Raman Spectroscopy Data for Lung Cancer Diagnosis," Analytical Chemistry, 2017, vol. 89, pp. 6695-6701.

Sina et al., "Real time and label free profiling of clinically relevant exosomes," Scientific Reports, 2016, vol. 6, Article No. 30460, pp. 1-9.

Stremersch et al., "Identification of Individual Exosome-Like Vesicles by Surface Enhanced Raman Spectroscopy," Small, 2016, vol. 12, No. 24, pp. 3292-3301.

Thakur et al., "Direct detection of two different tumor-derived extracellular vesicles by SAM-AuNIs LSPR biosensor," Biosensors and Bioelectronics, 2017, vol. 94, pp. 400-407.

Tirinato et al., "SERS analysis on exosomes using super-hydrophobic surfaces," Microelectronic Engineering, 2012, vol. 97, pp. 337-340.

Wang et al., "SERS Tags: Novel Optical Nanoprobes for Bioanalysis," Chemical Reviews, 2013, vol. 113, pp. 1391-1428.

* cited by examiner

COMPOSITIONS AND METHODS FOR THE DETECTION AND MOLECULAR PROFILING OF MEMBRANE BOUND VESICLES

CROSS-REFERENCE TO RELATED APPLICATION

This application claims the benefit of the following U.S. Provisional Application No.: 62/781,297, filed Dec. 18, 2018, the entire contents of which are incorporated herein by reference.

BACKGROUND OF THE INVENTION

Early detection of cancer increases treatment options and enhances survival rates. During early stages of the disease, cancer typically has not metastasized to tissues beyond the original tumor location or cell type, which makes the cancer susceptible to targeted therapies or even surgical removal. The five-year survival rate for women diagnosed with Stage I breast cancer 99% compared to only 27% for those diagnosed with Stage IV cancer. Regular screening for breast cancer (i.e., mammogram) can detect cancer up to two years before the tumor can be detected by manual breast exam. Still, only 61% of breast cancer cases are diagnosed at an early stage, and effective screening tests for early detection do not exist for many cancers.

Extracellular vesicles, and especially exosomes, have great potential for use in cancer detection and diagnostics due to their unique attributes. Exosomes are about 30-150 nm membrane-bound vesicles that are continuously released by virtually all cells into extracellular environment via exocytosis. These vesicles carry nucleic acids, proteins, and other molecules expressed or produced in their parental cells. Because the molecular contents of exosomes reflect the cells of origin, biomarkers present in the parental cells can be assessed by examining exosomes derived from those cells.

Analysis of molecular markers provides a powerful way for biomarker detection and discovery. For protein detection, exosomes have been mainly analyzed with bulk protein methods, such as conventional western blotting, enzyme-linked immunosorbent assay (ELISA), mass spectrometry, and some emerging techniques based on various physical and chemical mechanisms. However, tumor-derived exosomes in biofluids are mixed with a vast background of non-tumor exosomes from various tissues and hematopoietic cells. Extracting pure tumor-derived exosomes is impractical since tumors are heterogenous and many cancer markers are often present on normal cells. Thus, bulk methods are inherently contaminated with normal exosomes, which masks exosome heterogeneity and limits detection sensitivity. Particularly, bulk methods cannot quantify the fraction of target-specific exosomes and thus cannot inform the number of cancer exosomes in biofluids.

To more sensitively, precisely, and quantitatively probe tumor-derived exosomes in biofluids, molecular technologies at the single exosome level are needed. Single exosome molecular analysis is, however, extremely challenging because the amounts of antigens on individual exosomes is extremely low, down to single digit levels. Fluorescent imaging with dye molecules without signal amplification is very difficult due to the low sensitivity of dye molecules. Conventional flow cytometry is inaccurate due to the high background, false positives, and size limitation (flow cytometry typically works well with size >300 nm). In addition, the amount of sample required for clinical applications is very small and thus require low sample consumption technologies. For routine biomarker detection and quantification in the clinical settings, simple, efficient, and highly sensitive assays capable of analyzing small volumes of samples are needed. This disclosure is directed to these important technical needs.

SUMMARY OF THE INVENTION

As described herein, the present disclosure features compositions and methods related to the detection and profiling of extracellular vesicles (e.g., exosomes, microvesicles) at single exosome level using fluorescence nanoparticles, such as quantum dots and dye-coated magnetic nanoparticles. The present disclosure also features devices for the detection and profiling of extracellular vesicles.

In one aspect, the invention features an extracellular vesicle capture and detection system including (a) an extracellular vesicle containing a fluorescent probe, where the extracellular vesicle is bound to a capture molecule covalently bound to a film coating the planar support; (b) an array containing a plurality of holes, where the array is fixed to the film-coated surface of the planar support to form a plurality of fluid-tight wells; (c) a laser tuned to emit a wavelength that can effectively excite the fluorescent probe; and (d) a signal collection device for collecting a signal from the excited fluorescent probe.

In another aspect, the invention features an extracellular vesicle capture and detection system including (a) an array containing a plurality of fluid-tight wells, where the surface of each well is coated with a film containing one or more capture molecules covalently bound to the film; (b) an extracellular vesicle containing a fluorescent probespecifically bound to a capture molecule present on the film; (c) a laser tuned to emit a wavelength sufficient to excite the fluorescent probe; and (d) a signal collection device for collecting a signal from the excited fluorescent probe. In one embodiment, the planar support is a glass microslide, silicon wafer, or other planar surface. In another embodiment, the film is a gold or silver film. In another embodiment, the array is plastic, resin, rubber, or silicone. In another embodiment, the plurality of fluid-tight wells contains wells that are about 1 mm in diameter and the inter-well distance is at least about 0.5 mm to about 10 mm. In another embodiment, the capture molecule is an antibody, aptamer, or other molecule that specifically binds an antigen present on the surface of an extracellular vesicle. In another embodiment, the capture molecule is an antibody that specifically binds ALIX, TSG101, CD81, CD63, or CD9. In another embodiment, the capture molecule is a lipophilic composition. In another embodiment, the lipophilic composition contains a molecule having an alkyl chain and an affinity for a lipid bilayer of an extracellular vesicle. In another embodiment, the lipophilic composition is 1,2-distearoyl-sn-glycerol-3-phosphoethanoloamine conjugated polyethylene glycol thiol (DSPE-PEG-SH). In another embodiment, the fluorescent probe is a fluorescently labeled nanoparticle or a quantum dot. In another embodiment, the quantum dot is QD525, QD565, QD605, QD655, QD705, or QD800. In another embodiment, the fluorescently labeled nanoparticle is Magdye665 or Alexa Fluor 405.

In another aspect, the invention features a method for detectably labeling an extracellular vesicle, the method including (a) contacting an extracellular vesicle with a membrane tag containing a capture molecule; and (b) contacting the extracellular vesicle of step (a) with a fluorescent probe under conditions that permit binding of the capture molecule to the fluorescent probe, thereby detectably labeling the extracellular vesicle.

In another aspect, the invention features a method for characterizing an extracellular vesicle, the method including (a) contacting the extracellular vesicle with a primary antibody that specifically binds a biomarker present on the extracellular vesicle; (b) contacting the extracellular vesicle of step (a) with a secondary antibody that specifically binds the primary antibody, where the secondary antibody is conjugated to a first fluorescent probe; (c) exposing the extracellular vesicle containing the fluorescent probe to a wavelength sufficient to elicit a detectable signal from the fluorescent probe; and (d) detecting the presence or absence of a signal, thereby characterizing the extracellular vesicle.

In another aspect, the invention features a method for characterizing an extracellular vesicle, the method involving (a) contacting the extracellular vesicle with a primary antibody that specifically binds a biomarker present on the extracellular vesicle; (b) contacting the extracellular vesicle of step (a) with a secondary antibody that specifically binds the primary antibody, where the secondary antibody is conjugated to a first member of a binding pair; (c) contacting the extracellular vesicle of step (a) with a streptavidin-conjugated fluorescent probe (d) exposing the extracellular vesicle containing the fluorescent probe to a wavelength sufficient to elicit a detectable signal from the fluorescent probe; and (e) detecting the presence or absence of a signal, thereby characterizing the extracellular vesicle.

In another aspect, the invention features a method of monitoring treatment of a subject having or suspected of having a disease, the method involving performing the steps of any one of the previous aspects at a time point prior to treatment and at least one time point after treatment commences; comparing the initial amount of the second or third molecule to the amount of the second or third molecule after treatment commences; and adjusting the treatment protocol if the amount of the second or third molecule is different from the initial amount.

In another aspect, the invention features a labeled extracellular vesicle containing a membrane tag having a capture molecule bound to a fluorescent probe.

In another aspect, the invention features a labeled extracellular vesicle containing (a) a biomarker present on the extracellular vesicle; (b) a primary antibody bound to the biomarker present on the extracellular vesicle; and (c) a secondary antibody bound to the primary antibody, where the secondary antibody is conjugated to a first fluorescent probe.

In various embodiments of the above aspects, or any other aspect of the invention described herein, the fluorescent probe is a fluorescently labeled nanoparticle (e.g., Magdye665 or Alexa Fluor 405) or a quantum dot (e.g., QD525, QD565, QD605, QD655, QD705, or QD800). In various embodiments of the above aspects, or any other aspect of the invention described herein, the method further involves capturing the exosome with a capture molecule present on a substrate. In various embodiments of the above aspects, or any other aspect of the invention described herein, the substrate is a bead, membrane, wafer, chip, slide, or array. In various embodiments of the above aspects, or any other aspect of the invention described herein, the wavelength sufficient to elicit a visible signal from the first fluorescent probe is about 400 nm. In various embodiments of the above aspects, or any other aspect of the invention described herein, the steps of the method are carried out on the system of any previous aspect. In various embodiments of the above aspects, or any other aspect of the invention described herein, the signal detected is proportional to the amount of extracellular vesicles present in the sample. In various embodiments of the above aspects, or any other aspect of the invention described herein, the method further involves incubating the sample with a membrane tag containing a lipophilic moiety and a biotin moiety, where the lipophilic moiety adheres to the lipid membrane of the extracellular vesicle; and incubating the sample with a fluorescent probe, where the fluorescent probe contains a streptavidin molecule conjugated to a second fluorescent probe, and where the streptavidin molecule binds to the biotin moiety of the membrane tag to effectively label the extracellular vesicle with the fluorescent probe. In various embodiments of the above aspects, or any other aspect of the invention described herein, the wavelength sufficient to elicit a visible signal from the first fluorescent probe is sufficient to elicit a signal from the second fluorescent probe. In various embodiments of the above aspects, or any other aspect of the invention described herein, the signals emitted from the first and second fluorescent probes are different wavelengths. In various embodiments of the above aspects, or any other aspect of the invention described herein, the signal emitted from the second fluorescent probe is proportional to the amount of extracellular vesicles present in the sample. In various embodiments of the above aspects, or any other aspect of the invention described herein, the visible signal emitted from the first fluorescent probe is proportional to the amount of the molecule to be detected in the sample. In various embodiments of the above aspects, or any other aspect of the invention described herein, the method further involves:

incubating the sample with a second primary antibody that specifically binds a second molecule;

incubating the sample with a second secondary antibody that specifically binds the second primary antibody, where the second secondary antibody is labeled with a third fluorescent probe, and exposing the sample to a wavelength sufficient to elicit a visible signal from the third fluorescent probe, where the wavelength that effectively elicits a visible signal from the first and second fluorescent probe can effectively elicit a visible signal from the third fluorescent probe that is distinct from the visible signal elicited from the first and second fluorescent probe.

In various embodiments of the above aspects, or any other aspect of the invention described herein, the visible signal detected from the third fluorescent probe is proportional to the amount of the second molecule in the sample. In various embodiments of the above aspects, or any other aspect of the invention described herein, the signal elicited from the first, second, or third fluorescent probe, or any combination thereof, is collected by a charge-coupled device. In various embodiments of the above aspects, or any other aspect of the invention described herein, the signal is from a single exosome. In various embodiments of the above aspects, or any other aspect of the invention described herein, the signal elicited from the first, second, or third fluorescent probe, or any combination thereof, is collected by a spectrometer. In various embodiments of the above aspects, or any other aspect of the invention described herein, the signal collected is from more than one exosome. In various embodiments of the above aspects, or any other aspect of the invention described herein, the second molecule or third molecule or both is associated with a disease. In various embodiments of the above aspects, or any other aspect of the invention described herein, the amount of the second molecule or third molecule relative to a reference sample is correlated with disease severity or progression.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "alteration" is meant a change (increase or decrease) in an analyte as detected by methods such as those described herein. In one embodiment, the alteration is in the level of a protein biomarker present on a membrane bound vesicle. As used herein, an alteration includes a 10% change in expression levels, preferably a 25% change, more preferably a 40% change, and most preferably a 50% or greater change in expression levels.

An "aptamer," as used herein, refers to an oligonucleotide or polypeptide that specifically binds to a target molecule.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "capture molecule" refers to a molecule that specifically binds a target. In particular embodiments, the capture molecule is polypeptide, polynucleotide, or small molecule. In one embodiment, the capture molecule is an antibody or aptamer that specifically binds a protein on the surface of an extracellular vesicle. In another embodiment, the capture molecule is biotin and the target is streptavidin.

"Detect" refers to characterizing the presence, absence, or amount of an analyte in a sample.

By "detectable label" is meant a composition that when linked to a molecule of interest renders the latter detectable, via spectroscopic, photochemical, biochemical, immuno-chemical, or chemical means. For example, useful labels include quantum dots, radioactive isotopes, magnetic nano- or micro-particles, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Exemplary diseases that can be evaluated using a method of the invention include, but are not limited to, cancer and neurodegenerative diseases.

The term "exosome" refers to a cell-derived membrane bound vesicle comprising a membrane and lumen, wherein the exosome is typically between 30 and 100 nm in diameter. Exosomes, like other membrane bound vesicles, may contain surface bound or lumenal molecules that allow the identification of the cell type from which the exosome originated.

By "extracellular vesicle" is meant a membrane bound vesicle that is present extracellularly. Exemplary extracellular vesicles include exosomes and microvesicles.

By "fluid-tight" is meant capable of retaining a liquid sample for the duration of an assay without the sample leaking or seeping from a compartment or well.

By "fluorescent probe" is meant any reporter molecule that emits a detectable fluorescent signal when in an excited state.

By "fluorescently labeled nanoparticle" is meant a nanoparticle (e.g., a bead or metallic particle) that is labeled (e.g., conjugated, coated, or otherwise attached) with a fluorescent moiety (e.g., a fluorescent dye).

The term "lumenal molecule" refers to a molecule residing within the lumen of a membrane bound vesicle.

By "marker" is meant any biomolecule having an alteration in expression level or activity that is associated with a disease or disorder. A marker can be a protein, a polynucleotide, a lipid, or a carbohydrate.

By "membrane bound vesicle" is meant any vesicle comprising a membrane structure. Exemplary membrane bound vesicles include, but are not limited to, extracellular vesicles (e.g., microvesicles and exosomes) and apoptotic bodies. A membrane bound vesicle may comprise an exosome, and when the membrane bound vesicle fuses with the plasma membrane of a cell, it releases the exosome into the extracellular milieu.

By "membrane tag" is meant a composition comprising a lipophilic moiety bound to a linker bound to a moiety that can bind to or otherwise sequester a quantum dot. For example, a membrane tag may have a biotin moiety that is able to bind the streptavidin moiety of a streptavidin-labeled quantum dot. In one embodiment, the lipophilic moiety is cholesterol, the linker is PEG, and the moiety that binds the quantum dot is biotin.

The term "microvesicle" refers to vesicles originating from the plasma membrane of a cell. Microvesicles are typically larger than an exosome.

By "primary antibody" is meant an antibody having an affinity for an epitope on a molecule of interest.

"Quantum dot" (QD) refers to a probe made from nanocrystals of semiconductor material, wherein the probe can emit electromagnetic radiation. Generally, larger diameter quantum dots emit longer wavelength radiation than smaller diameter quantum dots. For example, quantum dots having a diameter of about 2 nm will have a visible emission farther in the blue region than a quantum dot having a diameter of about 5 nm. A quantum dot can also be tuned to emit a particular wavelength by changing the composition comprising the quantum dot or the structure thereof without changing the crystal size.

By "reduce" is meant a negative alteration of at least 10%, 25%, 50%, 75%, or 100%.

By "reference" is meant a standard or control condition. In some embodiments, a reference is the level of an analyte, marker, or other readout present in a corresponding control cell (e.g., an untreated cell, wild-type cell).

As used herein, "secondary antibody" refers to an antibody having an affinity for an epitope on a primary antibody. In some embodiments, a secondary antibody can comprise a label (i.e., a quantum dot).

By "subject" is meant a mammal, including, but not limited to, a human or a non-human mammal, such as a bovine, equine, canine, ovine, porcine, feline, or other domesticated mammal.

A "surface bound molecule" refers to a molecule that is bound to or integrated into the membrane of a membrane bound vesicle.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is an illustration of the formation of exosomes and the eventual release of the exosomes by cells after fusion of membrane bound vesicle (MBV) with the cell membrane. FIG. 1B is an illustration of a single exosome having a lipid bilayer and a lumen. FIG. 1C is an illustration of plasma from cancer patients comprising tumor-derived exosomes, non-cancer exosomes, and exosomes derived from hematopoietic cells.

FIG. 4A is a photograph of a standard microscope slide coated with Au film. FIG. 4B is schematic diagram of a 3D printed array cassette. FIG. 4C is a photograph of the chamber slide formed by the cassette and Au-coated glass slide.

FIG. 6A is a photograph showing fluorescing exosomes captured from a breast cancer patient plasma sample using an anti-CD81 capture antibody. FIG. 6B is a photograph showing fluorescing exosomes capture from a breast cancer patient plasm sample using an isotype IgG control. The fluorescence signals came from DiO dye that labels exosome membranes. The fluorescence signals came from DiO that labels exosome membranes.

FIG. 7A is an absorption spectrum graph illustrating the broad absorption ranges of QD525 and QD655. FIG. 7B is an emission spectrum graph illustrating the nonoverlapping emission spectra of QD525 and QD655, which give the distinctive fluorescent signals at the same excitation wavelength (400 nm).

FIG. 9A is a fluorescence image of MDA-MB-231 exosomes with dual color QD labelling (QD525 for membrane and QD655 for CD44 breast cancer protein marker). FIG. 9B is the emission spectrum generated from the data collected in FIG. 9A. FIG. 9C is a fluorescence image of MDA-MB-231 exosomes with dual color QD labelling, wherein a 600 nm long-pass filter blocks all visual signals except those emitted from exosomes labeled with QD655. FIG. 9D is a graph illustrating the bulk detection of visible signals emitted from a sample of labeled exosomes.

FIG. 10A shows the mask image of SKBR3 exosomes in detecting HER2 breast cancer protein marker labeled with Alex Fluor 405. FIG. 10B is the HER2-tageting image of the SKBR3 exosomes labeled with Magdye 665. FIG. 10C shows the mask image labeled with Alexa Fluor 405 of the negative control sample. FIG. 10D shows the HER2-targeting image labeled with Magdye of the negative control sample. The negative control is the lack of HER2 primary antibody during the labeling process.

FIG. 11A shows the original exosome mask and protein target images. FIG. 11B shows the step of background removal. FIG. 11C shows the normalization step. FIG. 11D shows the step of overlapping the mask and target images. FIG. 11E shows the signal extraction step.

DETAILED DESCRIPTION OF THE INVENTION

This disclosure features an innovative approach to detect and characterize ensemble and single extracellular vesicles, such as exosomes and microvesicles, by labeling and detecting molecular contents of the vesicles with fluorescent nanoparticles and detecting them in a dual imaging approach. The disclosures herein are based on novel exosome imaging, wherein fluorescent nanoparticles are used as the contrast agent to enhance detection of low level of surface protein antigens on single vesicles, particularly exosomes, and exosomes are localized by elastic light scattering imaging or fluorescence imaging with fluorescence probe. Because the molecular contents of exosomes reflect the cells of origin, the methods and compositions described herein can be used to identify diseased cells without time consumer pre-isolation of the extracellular vesicle. The fluorescent nanoparticles can be quantum dots (QDs), nanoparticles containing fluorescent dyes or any other nanoparticles with fluorescent properties.

Exosomes circulate in blood and many other body fluids, with typical concentration of $10^9$-$10^{11}$ vesicles/ml blood. The level and molecular profile of circulating tumor exosomes have been shown to correlate with tumor burden, and tumor-derived exosomes can transfer oncogenic factors to other cells to promote tumor growth and progression. Exosomes are generally stable and can tolerate multiple cycles of freezing and thawing while preserving structure and molecular contents for over five years when stored in liquid nitrogen. Thus, exosomes offer a robust source to discover blood-based biomarkers for clinical use.

Figure 1A:
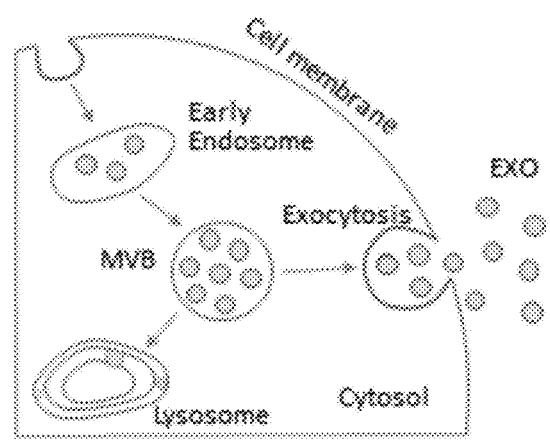
FIGS. 1A to 1C are illustrations of the formation and composition of exosomes and an example of an exosome population in cancer patient plasma.
Figure 1B:
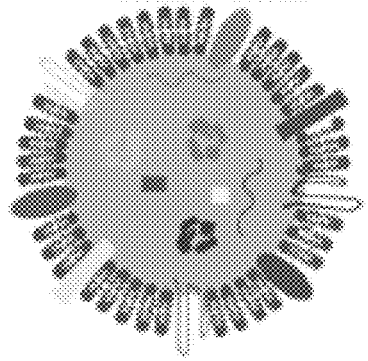

Exosomes originate in a cell and are eventually released directly from the cell into the extracellular milieu or they are released when the membrane bound vesicle in which they reside fuses with the plasma membrane of the cell (FIG. 1A). Referring to FIG. 1B, an exosome may comprise proteins, carbohydrates, lipids or other molecules on its surface (such as embedded in its lipid bilayer membrane). An exosome may also contain lipids, carbohydrates, proteins or nucleic acids in its lumen. In some instances, the nucleic acids in the lumen of the exosome include mRNA, miRNA, tRNA, rRNA, and DNA nucleic acids and proteins reflective of the cells of origin. In some embodiments, the proteins in the lumen of the exosome or associated with the exosome's membrane include, but are not limited to, tetraspanins, receptors, adhesion molecules, transporters, cytosolic proteins, and cytoskeleton proteins.

Figure 1C:
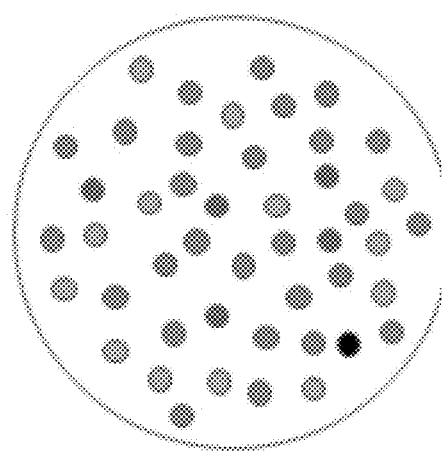

The molecules on the surface or in the lumen of an exosome can be indicative of the type of cell from which the exosome originated. Molecules associated with a disease may be excreted from a diseased cell in an exosome or other extracellular vesicles, and detection of such exosomes or other extracellular vesicles comprising the disease-associated molecules is evidence of a disease-state. In some instances, the molecule associated with a disease may be a marker for the disease. In other embodiments, the molecule is associated with a disease only when it is present in amounts that differ from a reference amount associated with a healthy state. For example, in some cases overexpression of a molecule that is present in healthy cells is indicative of disease. In some embodiments, a sample taken from a subject may comprise a heterogenous population of exosomes. Referring to FIG. 1C, plasma from cancer patients may contain exosomes derived from tumor cells, non-tumor cells, and hematopoietic cells.

Figure 2:
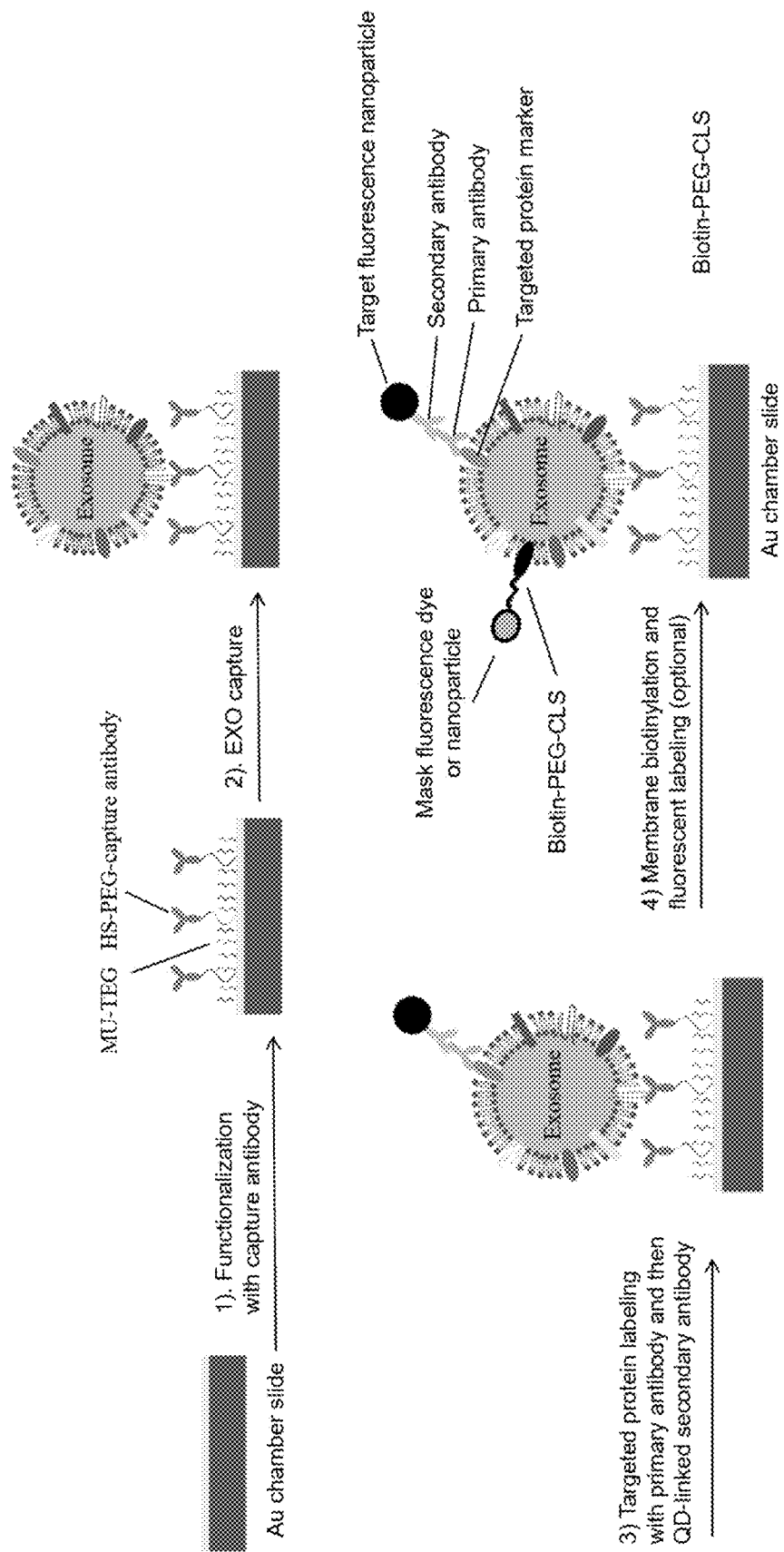
FIG. 2 is a schematic illustration of exosome capture and labeling with fluorescence nanoparticles. The methodology includes four steps: (1) functionalization of a gold (Au) coated glass slide with capture antibodies, (2) exosome capture on the Au-coated glass slide, (3) targeted protein labeling with a primary antibody and a fluorescent nanoparticle-onjugated secondary antibody, (4) (optional) mask membrane labeling with a fluorescent dye or nanoparticle via CLS-PEG-biotin lipophilic linker. The target fluorescent nanoparticle has different color from the mask fluorescent dye or nanoparticle. "CLS" denotes cholesterol. "PEG" denotes poly(ethylene) glycol. The fluorescent nanoparticle can be a quantum dot (QD) or any nanoparticle that is fluorescent or that contains fluorescent dyes.
Figure 3:
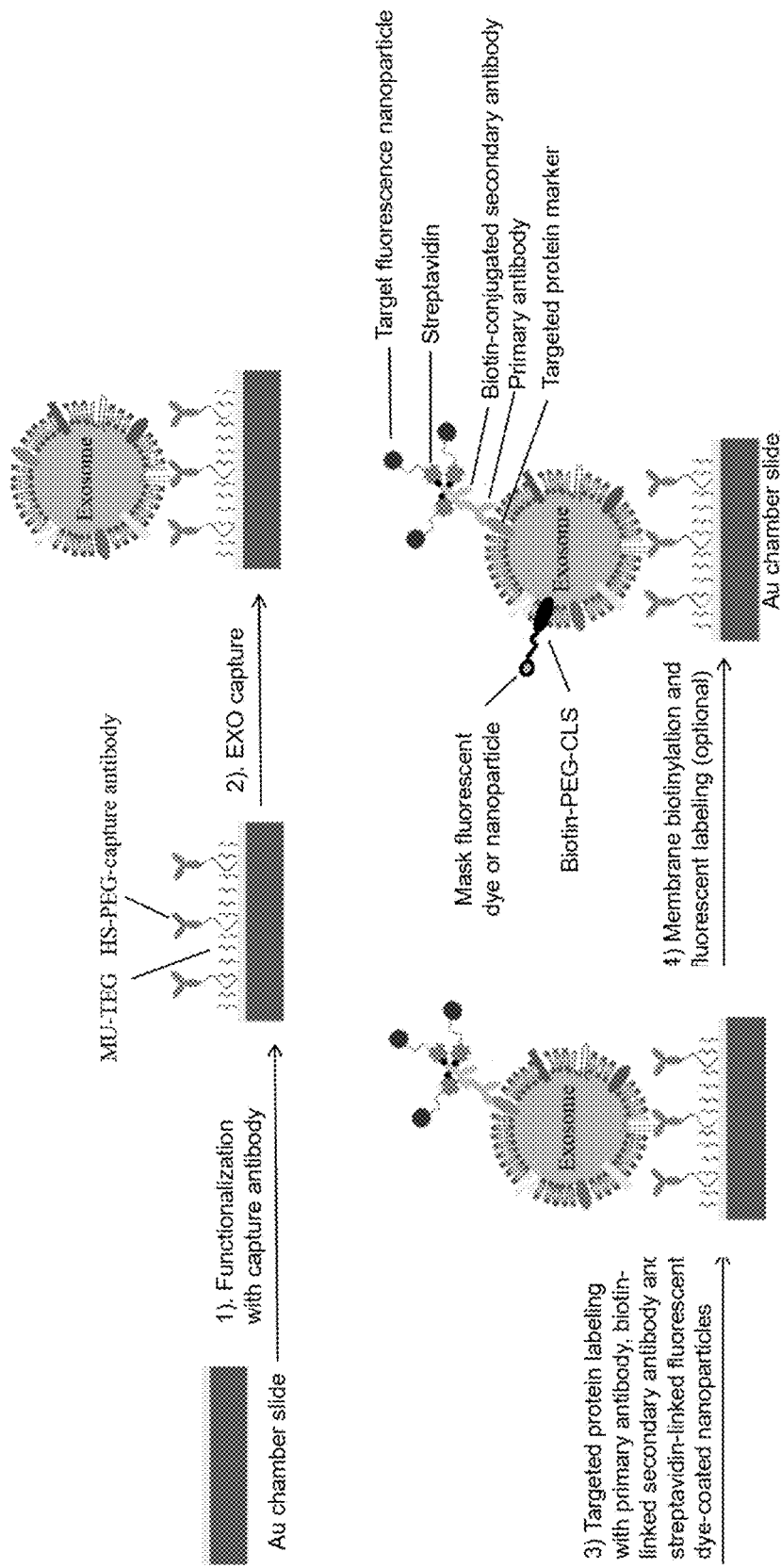
FIG. 3 is a schematic illustration of exosome capture and labeling with fluorescent nanoparticles and signal amplification. The methodology includes four steps: (1) functionalization of a gold (Au) coated glass slide with capture antibodies, (2) exosome capture on the Au-coated glass slide, (3) targeted protein labeling with primary antibody, biotin-conjugated secondary antibody, and streptavidin-conjugated fluorescent nanoparticle in a sequential order, (4) (optional) mask membrane labeling with a fluorescent dye or nanoparticle via CLS-PEG-biotin lipophilic linker. The target fluorescent nanoparticle has a different color from the mask fluorescent dye or nanoparticle. The fluorescent nanoparticle can be a QD or any nanoparticle that is fluorescent or contain fluorescent dyes. As each secondary antibody is linked with multiple biotins, multiple target fluorescent nanoparticles can be attached to the targeted protein to amplify signal readout.

In some embodiments of the present disclosure, extracellular vesicles can be isolated or captured by using a lipophilic capture agent. In other embodiments of the present disclosure, extracellular vesicles can be isolated or captured using an antibody having an affinity for the particular molecule on the surface of the extracellular vesicle to bind to the molecule (FIG. 2 and FIG. 3). Exosomes contain several proteins that differentiate them from other types of extracellular vesicles including microvesicles and apoptotic bodies. These proteins include ALIX, TSG101, and tetraspanins CD81, CD63, and CD9. The tetraspanins have been widely used as exosome markers to capture exosomes as they are found in a significant amount of exosomes from many different origins. For example, CD81 can be used as the exosome marker to capture exosomes. Other exosome markers such as CD9 and CD63 can also be used. The capture antibody having an affinity for the proteins associated with an exosome (or other extracellular vesicle) may be tethered to a substrate or bound to a second molecule (e.g., magnetic beads) that allows for isolation of the capture antibody-extracellular vesicle complex. For example, in some embodiments of the present disclosure, the capture antibody is tethered to a surface of an array. In some embodiments the capture antibody is a monoclonal antibody. In some embodiments, the antibody is a polyclonal antibody. When the antibody specific to tetraspanins is used, exosomes do not need pre-purification. Exosomes are diluted with phosphate buffer solution (PBS), filtered by size exclusion, and used directly for capture and detection.

In some embodiments of the present disclosure, the exosomes are captured in a chamber slide (FIG. 4). In some embodiments, the chamber slide contains a glass slide coated with Au film and a 3D printed array cassette. In some embodiments, the device contains over 100 wells for simultaneous multiple analyses.

Figure 5:
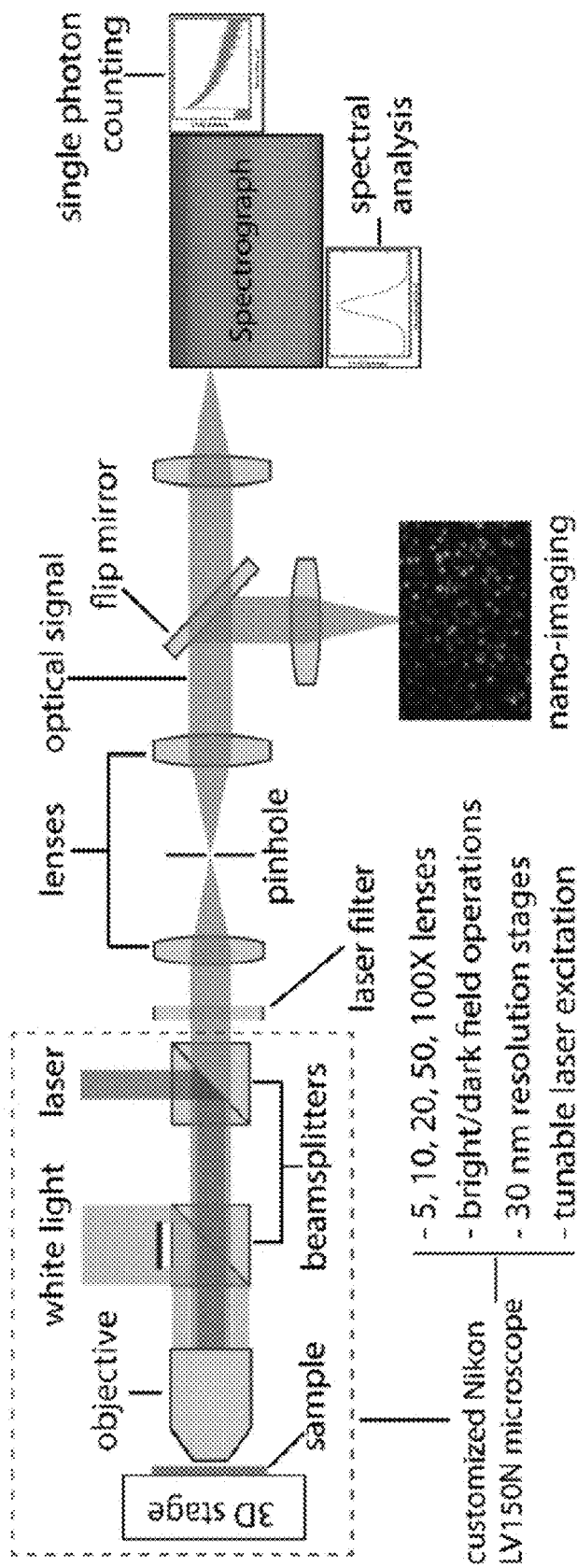
FIG. 5 is a schematic diagram of an integrated single particle microscopic optical system for immunofluorescence imaging and spectroscopic detection of exosomes.

In some embodiments of the present disclosure, an integrated single particle microscope is used to image exosomes (FIG. 5). In some embodiments, a confocal fluorescence microscope is used. In some embodiments, a regular fluorescence microscope is used to examine the existence of exosomes.

Figure 7A:
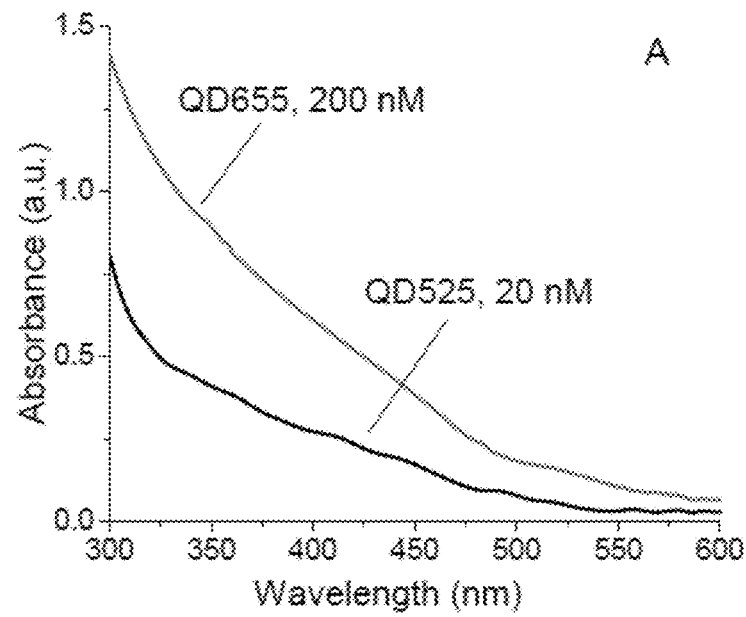
FIGS. 7A and 7B show the excitation and emission of two color QDs.

In some embodiments of the present disclosure, a QD probe is used to label proteins of interest (e.g., cancer markers) on the exosome membrane or within the lumen of the exosome. In some embodiments, a second QD probe is used to label an exosome's membrane. The visible signals emitted from the first and second QD probes are different wavelengths (See, for example, FIGS. 7A and 7B). Using two different QD probes (two-color imaging) in conjunction with a laser microscopy system or a confocal microscope and high throughput chamber slide, or array, a panel of cancer-relevant protein markers on and inside exosomes can be screened by both spectroscopic bulk measurements and by imaging-based single exosome analysis. In some embodiments, the exosome membrane is not labeled, and exosomes are imaged directly in dark field to localize exosomes.

Figure 8:
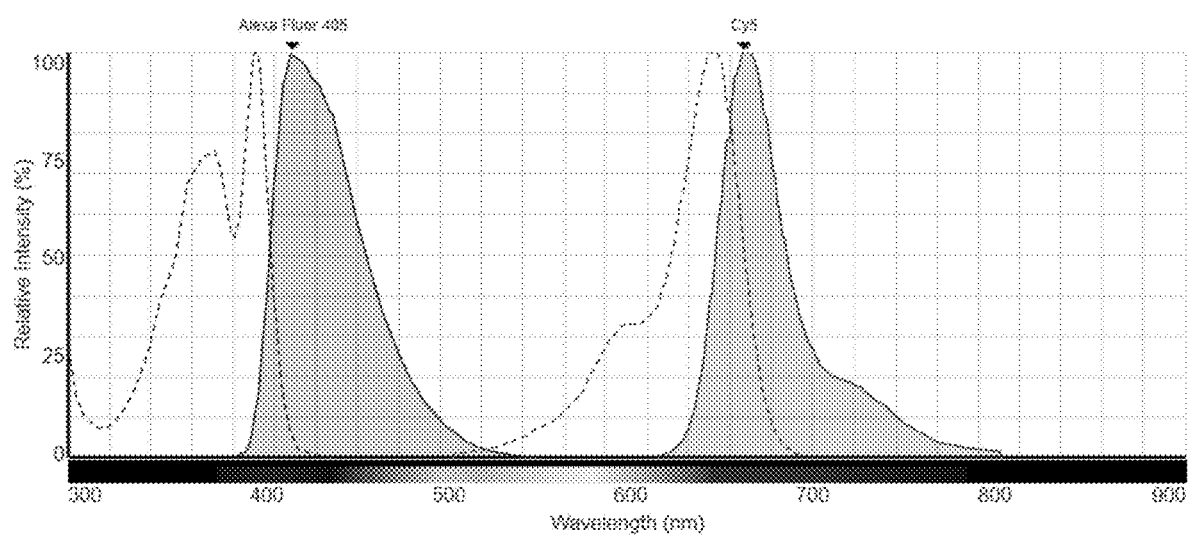
FIG. 8 shows the excitation and emission of two-color fluorescent dyes. In this figure, Alexa Fluor 405 serves as the mask labelling agent and Cy5 as the target labelling agent. The mask dye binds to exosome membrane to image and localize exosomes. The target dye labels the targeted protein marker to detect, image, and quantify the protein marker. The emission spectra of the two dyes are separated and thus do not interfere each other.

In some embodiments of the present disclosure, a magnetic nanoparticle coated with fluorescent dye is used to label proteins of interest (e.g., cancer markers) on the exosome membrane or within the lumen of the exosome. In some embodiments, a second dye is used to label an exosome's membrane. The visible signals emitted from the first and second dyes are different wavelengths (FIG. 8). Using two different dyes (two-color imaging) in conjunction with a laser microscopy system or a confocal microscope and high-throughput chamber slide, or array, a panel of cancer-relevant protein markers on and inside exosomes can be screened by both spectroscopic bulk measurements and by imaging-based single exosome analysis. In some embodiments, the exosome membrane is not labeled, and exosomes are imaged directly in dark field to localize exosomes.

In some embodiments of the present disclosure, signal detection is further enhanced by binding multiple fluorescent nanoparticles to a targeted protein (FIG. 3). In some embodiments, the secondary antibody is linked with multiple biotins to bind multiple fluorescent nanoparticles via streptavidin that is conjugated onto the fluorescent nanoparticle.

In some embodiments of the present disclosure, a single exosome dual imaging analysis (SEDIA) method is used to analyze the images (FIGS. 11A-11E). The method involves four major steps: 1) remove background noise of both mask and target images using a selected baseline removal algorithm; 2) re-normalize all intensities in both images against a maximum value (the user have the options to set the maximum value in order to fine-tune the identification of algorithm based on the mask (dark field image), and the Raman signals over the identified locations are obtained from the background-removed target image, 3) overlay two images to determine locations of exosomes, and 4) to extract Raman signals automatically to build a histogram. Using the single exosome analysis, small populations of cancer-derived exosomes in a vast background of non-cancer derived exosomes can be detected that would be are undetectable by the bulk methods currently known in the art. The fraction of tumor-derived exosomes, which are very important in cancer diagnostics and monitoring, can be quantified using this method. Exosome subpopulations can be identified and the exosome compositional heterogeneity can be discerned using the methods provided within. This information will be valuable for betting understanding tumor heterogeneity and help personalized treatment. Compared to the traditional Image J method, SEDIA is 20 times faster in terms of the overall time needed to process a pair of mask and target images.

The methods provided in the present disclosure only require submicroliter volumes of diluted plasma sample per marker. Over 200 samples can be processed on an array no bigger than a standard microscope slide, and the analysis is complete of a sample is complete in seconds. Therefore, compared to existing methods (including existing liquid biopsy protocols), the presently disclosed methods have several major advantages. The disclosed methods focus on single vesicle analysis but can also be used for bulk measurement via spectroscopic detection. The methods are highly sensitive, due to the use of fluorescent nanoparticles that are orders of magnitude brighter than fluorescent dyes. The methods are simple—capturing exosomes directly from plasma samples, labeling exosome membranes and the target protein with fluorescent probes that emit different visible signals, and detecting these signals with a facile optical system. The disclosed methods are also very efficient, capable of processing over 200 samples on a single slide, conducting each measurement within seconds, and analyzing data with high automation. Lastly, the presently disclosed methods require very small amounts of samples (i.e., submicroliter of plasma samples (typically 100 times dilution for a plasma sample)).

Extracellular Vesicle Sample Preparation

Extracellular vesicles such as exosomes may be found in any bodily fluid including, but not limited to, whole blood, plasma, ascites, breast milk, saliva, urine, sweat, semen, cerebrospinal fluid, and ocular fluid. In some embodiments, collected bodily fluids containing extracellular vesicles are processed to remove cells, debris, larger vesicles, and other matter that may confound detection of the extracellular vesicles. For example, samples may be filtered to remove the potentially confounding matter. In some embodiments, the samples may be centrifuged to remove the potentially confounding matter. In some embodiments, the sample comprising extracellular vesicles are tested without any pre-analysis processing. In some embodiments, the samples comprising extracellular vesicles are diluted prior to analysis. Diluting the samples may allow for sufficient sample volume for testing on a multi-well array.

Arrays for Detecting and Characterizing Extracellular Vesicles

Figure 4A:
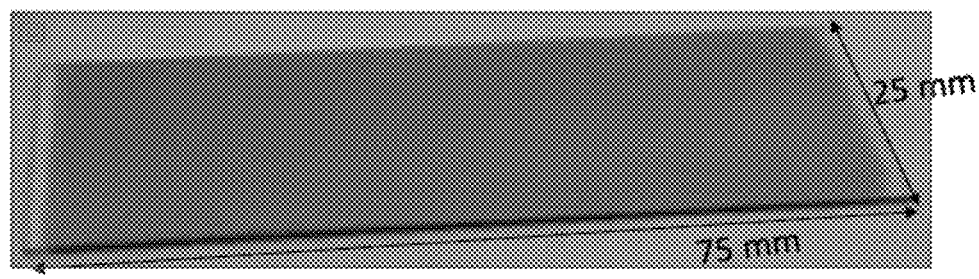
FIGS. 4A to 4C are photographs and schematic diagrams of the stages of fabrication of a multi-well array.
Figure 4B:
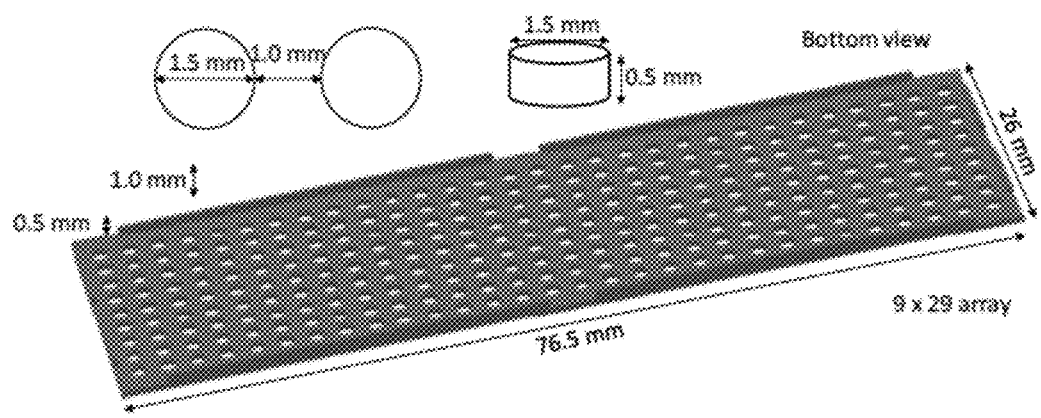
Figure 4C:
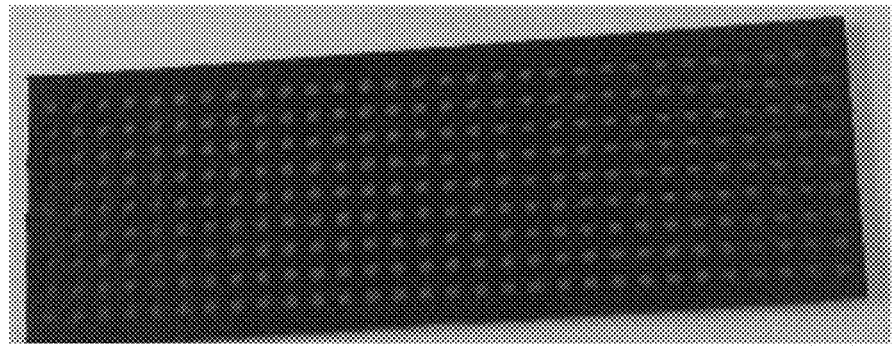

In some aspects of the present disclosure, a device is provided for the parallel processing and detection of extracellular vesicles in a plurality of samples (FIGS. 4A-4C). In some embodiments, the device comprises substrate having a functionalized surface to which capture antibodies are tethered. In some embodiments, the substrate is a glass slide coated with a substance that allows subsequent functionalization of the slide. For example, in some embodiments, the surface of the slide is coated with a gold film. The gold film can be between 1 and 200 nm thick. In some embodiments, the gold film is about 10 nm thick. In some embodiments, the gold film is optically transparent. A slide comprising a gold film surface can be fabricated using a magnetron sputtering technique that deposits a thin film of gold atoms onto a standard glass slide (i.e., 75 mm long×25 mm wide×1 mm thick). The gold surface of the slide may facilitate chemical modification of the slide's surface.

The slide may be functionally divided into two or more analytical zones where multiple samples can be analyzed in parallel. For example, the slide may be functionally divided into wells, and each well represents an analytical zone on the array. In some embodiments, the wells are formed by overlaying onto the slide a plastic (or other polymer) array having multiple holes. The array may be fabricated with a 3-D printer or any other available means (e.g., machined). Once overlaid, the holes on the array form the sample wells. To ensure tight fit of the array and the slide, pressure grease may be used to seal the array to the slide. In some embodiments, a gasket is situated between the slide and the array.

Figure 6A:
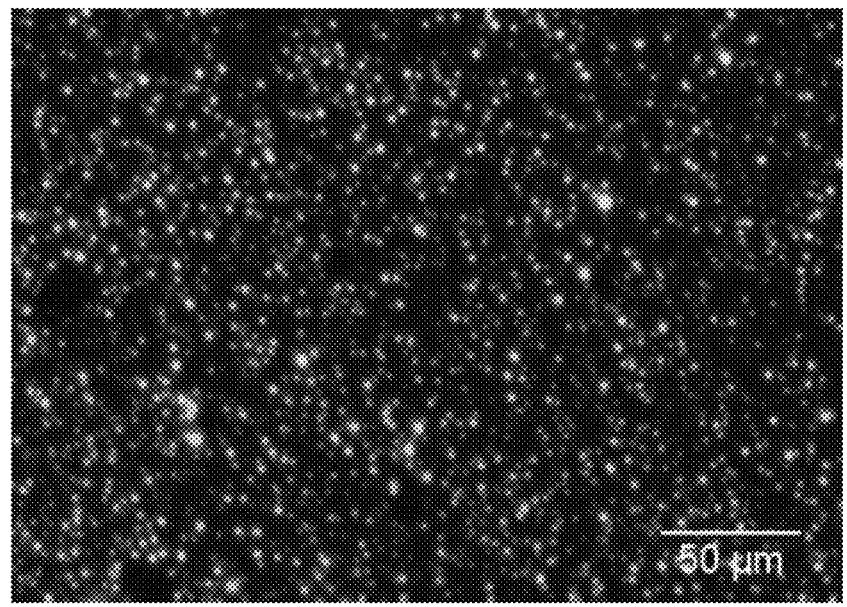
FIGS. 6A and 6B are photographs of captured exosomes and a control sample, respectively.

In some embodiments, the bottom surface of the well comprising the gold-coated film, is treated with a compound that reduces or eliminates nonspecific binding of the capture molecule (FIG. 2 and FIG. 3). In some embodiments, the compound that reduces or eliminates nonspecific binding is 11-mercaptoundecyl tetra (ethylene glycol) (MU-TEG), or a similar compound. Capture antibodies may be tethered to the substrate's functionalized surface. In some embodiments, the capture molecule is modified to facilitate binding to the functionalized surface of the substrate. For example, in some embodiments, the capture molecule is linked to a polyethylene glycol thiol (PEG-SH, molecular weight=5,000 kDa). The specific capture of exosomes directly from blood with the capture molecules was confirmed with fluorescence imaging. FIG. 6A shows an example when CD81 antibodies were used as the capture molecule compared to the control with isotype IgG that was not able to capture exosomes.

In other embodiments, extracellular vesicles are isolated or captured by using a lipophilic chemical layer on the surface of the array. Lipophilic molecules comprising an alkyl chain have high affinity for the lipid bilayer of molecules (i.e., extracellular vesicles) through hydrophobic interactions between the lipid membrane of the extracellular vesicle and the lipophilic molecules on the substrate. In some embodiments, the lipophilic molecule is 1,2-distearoyl-sn-glycerol-3-phosphoethanoloamine conjugated polyethylene glycol thiol (DSPE-PEG-SH; molecular weight=5,000 kDa). The thiol group binds the DSPE-PEG-SH to the gold film on the surface of the slide, and the DSPE portion of the lipophilic molecule binds to the extracellular vesicle's membrane. Again, MU-TEG can be used to saturate the gold film surface of the array to reduce or eliminate nonspecific binding.

Detection methods may include use of a biochip array. Biochip arrays useful in the invention include protein and polynucleotide arrays. One or more markers are captured on the biochip array and subjected to analysis to detect the level of the markers in a sample.

Markers may be captured with capture reagents immobilized to a solid support as described herein, such as a biochip, a multiwell microtiter plate, a resin, or a nitrocellulose membrane that is subsequently probed for the presence or level of a marker. For example, a sample containing EXOs may be used to contact the active surface of a biochip for a sufficient time to allow binding. Unbound molecules are washed from the surface using a suitable eluant, such as phosphate buffered saline. More stringent eluants remove proteins that are not tightly bound.

Upon capture on a biochip, analytes can be detected by the Raman-based spectroscopy methods as described herein. In some embodiments, the analytes can be detected by additional methods as well. In one embodiment, optical methods, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry) are used. Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Antibodies that specifically bind polypeptides and nucleic acid molecules present in EXOs may be used as hybridizable array elements in a microarray. The array elements are organized in an ordered fashion such that each element is present at a specified location on a substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Protein Microarrays

Proteins may be analyzed using protein microarrays. Such arrays are useful in high-throughput low-cost screens to identify alterations in the expression or post-translation modification of a polypeptide of the invention, or a fragment thereof. In one embodiment, a protein microarray as contemplated herein binds a marker present in a subject sample. Alterations in the level of the marker can be detected. In some embodiments, the protein microarray features a capture agent, such as an antibody or fragment thereof, bound to a solid support. Suitable solid supports include membranes (e.g., membranes composed of nitrocellulose, paper, or other material), polymer-based films (e.g., polystyrene), beads, or glass slides. The surfaces of these solid supports may be functionalized as described herein. For some applications, capture agents (e.g., antibodies that bind a marker of the invention) are spotted on a substrate using any convenient method known to the skilled artisan (e.g., by hand or by inkjet printer). The capture agents specifically bind to extracellular vesicles.

After the array is contacted with samples comprising extracellular vesicles, the protein microarray is hybridized with a detectable probe. Such probes can be polypeptide, nucleic acid molecules, antibodies, or small molecules labeled with a quantum dot. Probes can include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions, and such conditions are known to the skilled artisan and are described, for example, in Harlow, E. and Lane, D., Using Antibodies: A Laboratory Manual. 1998, New York: Cold Spring Harbor Laboratories. Unbound probes are removed and specifically bound probes are detected, for example, by fluorescence, enzyme activity (e.g., an enzyme-linked calorimetric assay), direct immunoassay, radiometric assay, or any other suitable detectable method known to the skilled artisan.

Quantum Dot Probes for the Detection of Extracellular Vesicles

The present disclosure provides methods of detecting and characterizing extracellular vesicles by using high throughput array and quantum dot (QD) probes. QD probes comprise a molecule having an affinity for a molecule of interest and a quantum dot. QDs have broad excitation wavelength wave compared to traditional fluorescent dyes, yet have a narrow emission wavelength and a large Stokes shift. Due to these properties, a single excitation source (i.e., a laser) can elicit strong signals from different QDs. In comparison, a single excitation source used with traditional fluorescent dyes may not sufficiently excite some dyes that have excitation spectra that do not include the excitation source's wavelength. Because only a single excitation source is required, the methods and compositions described herein provide a less expensive, more efficient means of detecting extracellular vesicles.

Examples of QDs include QD525, QD565, QD605, QD655, QD705, and QD800 (Invitrogen). QD525 has an emission maximum of about 525 nm (i.e., a visible green signal) and can be sufficiently excited by a wavelength about 400 nm to about 488 nm (FIG. 7). QD565 has an emission maximum of about 565 nm and can be sufficiently excited by a wavelength between about 350 nm and about 525 nm. QD605 has an emission maximum of about 605 nm and can be sufficiently excited with a wavelength between about 350 nm and about 600 nm. QD655 has an emission maximum of about 655 nm (i.e., a visible red signal) that can be sufficiently excited with a wavelength between about 350 nm and about 615 nm. QD705 has an emission maximum of about 705 nm and can be excited with a wavelength about 350 nm to about 630 nm. QD800 has an emission maximum of about 800 nm and can be excited with a wavelength about 350 nm to about 630 nm. Each QD can be excited using a laser that emits a wavelength sufficient to elicit a significant range (about 525 nm to about 800 nm) of possible emission maximums. In some embodiments, the laser is tuned to emit a 400 nm wavelength. In some embodiments, the laser is a 405 nm laser, 488 nm laser or other monochromatic commercially available laser with a wavelength from 400 to 500 nm. For example, because the emission maximums of the QD525 and the QD655 are distinct, both probes can be used to simultaneously detect two different molecules in a sample. For example, green QD525 can be used to detect a protein or other molecule that is only present in the lumen of an extracellular vesicle, while red QD655 can be used to detect a protein or other molecule that is only present on the surface of an extracellular vesicle. This is also true for all combinations of the QDs.

Quantum Dot Labeling of Extracellular Vesicles

The methods disclosed herein contemplate detecting extracellular vesicles by labeling the vesicles with a QD probe. In some embodiments, an antibody having an affinity for an epitope on an extracellular vesicle is conjugated to a QD. By incubating a sample comprising extracellular vesicles with the antibody conjugated to a QD, the antibody will bind to the epitope, thereby detectably labeling the extracellular vesicle.

Other methods of labeling extracellular vesicles are contemplated herein. For example, in some embodiments, extracellular vesicles, such as exosomes, are tagged with a composition that facilitates downstream labeling. In some embodiments, the tag comprises a lipid moiety that can be integrated into an extracellular vesicle's membrane. In some embodiments, the tag also comprises a moiety that can be recognized and bound by a composition comprising a detectable label. In some embodiments, the tag is a cholesterol-polyethylene glycol-biotin (CLS-PEG-biotin) tag. Samples containing extracellular vesicles can be incubated with CLS-PEG-biotin tags, wherein the cholesterol moiety of the CLS-PEG-biotic tag becomes integrated into the extracellular vesicle's membrane.

The samples comprising tagged extracellular vesicles can be detectably labeled. Detectable labels, as contemplated herein, comprise a moiety that can recognize and bind to the extracellular portion of the tag that is integrated into an extracellular vesicle's membrane. For example, if the tag comprises a biotin moiety, then the detectable label may comprise streptavidin, which binds to biotin. The detectable label also comprises a quantum dot probe. For example, the detectable label may be QD655-labeled secondary antibody or streptavidin. In some embodiments, the sample comprising an extracellular vesicle having a CLS-PEG-biotin tag is incubated with a quantum dot-labeled streptavidin that recognizes and binds to the biotin moiety of the CLS-PEG-biotin tag. In some embodiments, the QD-labeled streptavidin allows detection of individual extracellular vesicles. In some embodiments, the quantum dot-labeled streptavidin allows detection of sample wells on an array comprising a sample having at least one extracellular vesicle.

In some embodiments, the slide wells are subsequently incubated with a primary antibody having an affinity for an epitope of a molecule on the surface of the extracellular vesicle, a molecule in the lumen of the extracellular vesicle, or both. In some embodiments, the molecule on the surface of the extracellular vesicle and the molecule in the lumen of the extracellular vesicle are the same molecule or related molecules. In some embodiments, the molecule on the surface of the extracellular vesicle is different than the molecule in the lumen of the extracellular vesicle. In some embodiments, the molecule on the surface of the extracellular vesicle, in the lumen of the extracellular vesicle, or both is a marker that is associated with an extracellular vesicle, thereby allowing positive identification of a sample well comprising an extracellular vesicle. In other embodiments, the molecule on the surface of the extracellular vesicle, in the lumen of the extracellular vesicle, or both is associated with a disease or condition or is indicative of from what cells or tissues the extracellular vesicle is derived.

Referring to the approach described in FIGS. 2 and 3, one embodiment of the methods for detecting an exosome provides capturing and labeling a surface bound molecule as well a particular molecule within the lumen of the extracellular vesicle. A capture molecule having a polyethylene glycol thiol (PEG-SH) linker is attached to the Au-coated slide by forming an Au—S bond. The gold (Au)-coated glass slide comprising the linked capture antibodies is then treated with 11-mercaptoundecyl tetra (ethylene glycol) (MU-TEG) to reduce or eliminate nonspecific binding to the surface of the slide. The slide is then exposed to a sample comprising extracellular vesicles. In this figure, the extracellular vesicle comprises both a targeted surface marker and a targeted internal marker. Molecules present on the surface of the extracellular vesicle are recognized and bound by the capture molecule, thereby immobilizing the extracellular vesicle on the array.

The array is next contacted with a primary antibody comprising at least one constant region and at least one variable region, wherein the variable region has complementary determining regions (CDRs) that can recognize and bind to a surface bound molecule on the extracellular vesicle. The primary antibody may be polyclonal or monoclonal. Additionally, the antibody may be an isolated, naturally occurring antibody. Conversely, the antibody may be engineered. The surface bound molecule for which the primary antibody has an affinity may be a protein, lipid, polysaccharide or other carbohydrate, or any other molecule residing on or in the extracellular vesicle's membrane. The surface bound molecule may be associated with a specific type of cell, which would allow one skilled in the art to determine from what type of cell the extracellular vesicle is derived. In some instances, the surface bound molecule may be associated with health status. For example, a vesicle having a surface bound molecule that is a cancer antigen would indicate that the cell from which the vesicle derived is cancerous. Conversely, some surface bound molecules may be associated with a normal state. In still other embodiments, the absence of a particular surface bound molecule may be indicative of a disease state. And in some embodiments, the absence of a surface bound molecule may be indicative of the absence of circulating tumor cells (or at least a concentration of circulating tumor cells that is so low as to avoid detection). In still other embodiments, the absence of a surface bound molecule that is associated with a normal physiological state may indicate a genetic or acquired condition that prevents or reduces the expression of the surface bound molecule.

In some embodiments, the primary antibody that recognizes and binds to the surface bound molecule is labeled with a quantum dot probe. In some embodiments, the primary antibody does not comprise a quantum dot probe. A sample in which a primary antibody without a quantum dot binds a surface bound molecule may be subsequently incubated with a secondary antibody comprising a quantum dot probe. This secondary antibody comprises at least one constant region and at least one variable region, wherein the variable region comprises complementary determining regions (CDRs) having an affinity for the primary antibody. In some embodiments, the secondary antibody will have an affinity for a constant region of the primary antibody.

Referring again to FIGS. 2 and 3, lumenal molecules can also be assessed using the methods disclosed herein. As with labeling surface bound molecules, lumenal molecules may be recognized and bound by a primary antibody having an affinity for the molecule. In some embodiments, the antibody is labeled with a quantum dot probe. In some embodiments, the primary antibody is not labeled with a detectable probe.

In some embodiments, a sample is interrogated for the presence, absence, or amount of both surface bound molecules and lumenal molecules. In some embodiments, the surface bound molecule and the lumenal molecule are different. For example, in some embodiments, the surface bound molecule is a protein, while the lumenal molecule is a nucleic acid. In some embodiments, the surface bound molecule and the lumenal molecule are the same type of molecule, but are distinct species. For example, in some embodiments, the surface bound molecule and the lumenal molecule are both proteins, but the surface bound protein is a receptor, while the lumenal protein is a structural protein associated with the cell from which the vesicle is derived. In embodiments in which surface bound molecule and the lumenal molecule are different, the quantum dot probe for detecting the surface bound molecule may be different from the probe that is used to detect the lumenal molecule. In some embodiments, wherein the surface bound protein and the lumenal protein are the same, the quantum dot probes used in their detection may be the same as well. Additionally, the methods and compositions comprised herein also contemplate the simultaneous detection of multiple lumenal and/or surface bound molecules. Some embodiments of the present disclosure provide for multiple distinct quantum dot-labeled antibodies, each recognizing and binding to a different surface bound or lumenal molecule or a different primary antibody that is bound to a different surface bound or lumenal molecule. The system can be effectively tuned as described above.

Referring to approach described in FIG. 3, every procedure is the same as FIG. 2 except the target protein labeling. In this approach, targeted primary antibody is recognized with a biotin-conjugated secondary antibody that will be subsequentially recognized with streptavidin-conjugated QDs. Compared to approach in FIG. 2, the signals are further enhanced because multiple target QDs can be bound to one secondary antibody due to the presence of multiple biotin ligands on the secondary antibody.

Detecting Quantum Dot-Labeled Extracellular Vesicles and Molecules

Detection of QD-labeled extracellular vesicles and molecules requires an excitation source and an emission collector. In some embodiments, the excitation source used to excite the QD probes is a laser. Because QDs have broad excitation spectra, the excitation source can be a single laser rather than a matched-laser system, wherein separate lasers with different wavelengths are required to efficiently excite the probes. In detection schemes using traditional fluorescent dyes, a single laser may be able to elicit emissions from two different dyes, but at least one of the dyes will have a reduced emission because the laser wavelength is not near the excitation wavelength maximum of the fluorescent dye. Reducing the componentry of the detection apparatus, reduces the cost of the machinery necessary to perform the methods described herein.

Commercially available or custom built confocal fluorescence microscope systems may be used to detect labeled extracellular vesicles. Referring to FIG. 3, which depicts a custom fluorescence microscope system, a laser is used to excite a sample on the 3D stage. In some embodiments, the laser is a tunable laser. Reflected fluorescent signal from the sample is collected by the objected and, after passing through the beam splitters, is filtered by an appropriate long-pass filter (to block the laser excitation) and refocused onto an intermediate image plane where a small pinhole is used to select single extracellular vesicles of interest. A series of lenses filters process the emitted signals allowing both nano-imaging of the fluorescing extracellular vesicles as well as capture by a spectrometer. A nano-image (typically captured by a charged couple device (CCD)) of fluorescing extracellular vesicles provides a qualitative visual image of the single vesicles present in a sample. In some embodiments, the spectrometer data provides a quantitative characterization of the detected extracellular vesicles (i.e., bulk analysis of the vesicles in the sample). The spectrometer and CCD camera are optimized for the visible frequency with up to 95% quantum efficiency that is ideal for single extracellular vesicle measurements.

Figure 9A:
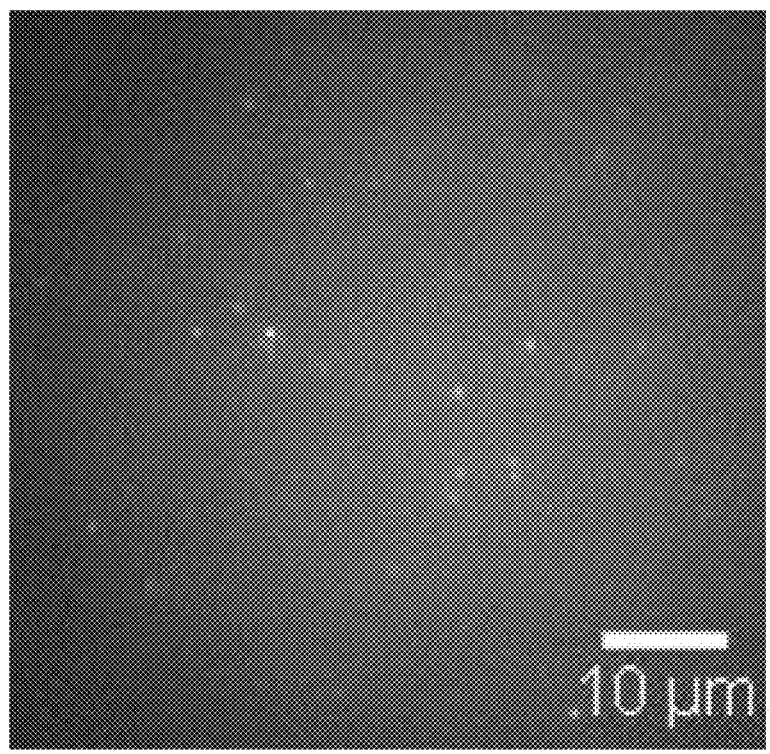
FIGS. 9A to 9D are images of collected data and graphs summarizing the data collection using QDs.
Figure 9B:
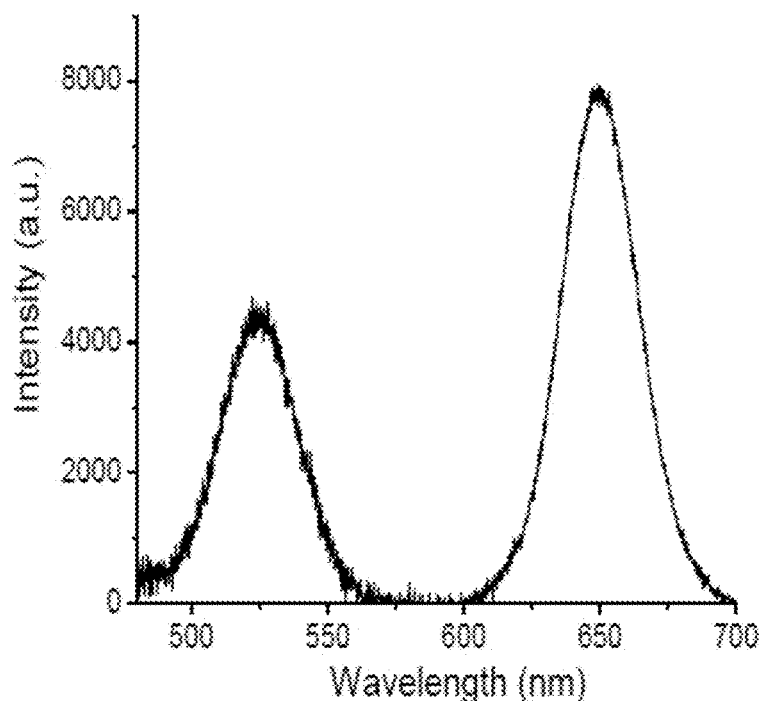

FIGS. 9A and 9B give an example of data collection. In this example, CD44 breast cancer marker on MDA-MB-231 exosomes was labeled with QD655-secondary antibody. Exosome membrane was labeled with streptavidin-QD525. Exosomes were localized via fluorescence image without 600 nm long-pass filter (FIG. 9A and FIG. 9B). CD44 on exosomes was detected when 600 nm long-pass filter was used to cut off signals from mask QD525 probes.

Magdye Labeling and Detection of Extracellular Vesicles

Fluorescent nanoparticles other than QDs can also be used to detect the low abundance of exosome surface proteins. One example is Magdye that comprises magnetic nanoparticles (10 to 100 nm) coated with multiple fluorescent dyes such as Cy5 (commercially available at Ocean Nanotech, LLC). The Magdye can be 300 times brighter than the dye itself due to the large number of dyes coated on the nanoparticles. The exosome labeling method using Magdye is the same as described as QDs above. For mask imaging, exosomes can be directly imaged in dark field without further labeling or imaged under fluorescence microscope after membrane labeling with a second dye with different color. An example is target imaging with Cy5 and membrane labeling with Alex Flor 405. The two dyes have separated emission properties and thus do not interfere each other (FIG. 8). Any other dual-color dyes can also be used provided that their excitation and emission spectra do not overlap.

FIGS. 10A-10D are examples of data collection. In these example, HER2 breast cancer marker on SKBR3 exosomes was labeled with Magdye 665 (www.oceannanotech.com/products-type/magdye/magdye-nanoparticles/streptavidin/665.html). Exosome membranes were labeled with Alexa Fluor 405. Exosomes were imaged with a regular confocal microscope.

Single Exosome Dual Imaging Analysis (SEDIA)

In some embodiments, the dual images (mask and target images) are analyzed with Image J (imagej.nih.gov/ij/features.html). In some embodiments, the mask-target images are analyzed using a Single Exosome Dual Imaging Analysis (SEDIA) software developed by the inventors. The SEDIA is 20 times faster than Image J, which dramatically enhances the efficiency of data analysis. The SEDIA allows for identification of individual exosome and obtaining Raman signal intensity integrated over the exosome area. FIGS. 11A-11E show an example of SEDIA while analyzing HER2 expression on SKBR3 exosomes. The analysis starts with a pair of mask image (exosome membrane labeling with Alexa Fluor 405) and target image (HER2 labeling with Magdye665-streptavidin) obtained over the same physical location on the sample. The process then follows four major steps: 1) remove background noise of both mask and target images using a selected baseline removal algorithm; 2) re-normalize all intensities in both images against a maximum value (the user have the options to set the maximum value in order to fine-tune the identification of algorithm based on the mask (dark field image) and the Raman signals over the identified locations are obtained from the background-removed target image; 3) overlay two images to determine locations of exosomes; and 4) extract Raman signals automatically to build a histogram. Locations of exosomes are identified using peak-finding inspection of individual spot, if needed, by the user to determine if the spot is an exosome or an artifact due to imperfections on the plate.

After the manual inspection by the user, the Raman intensity over the exosome spot (integrated within approximately 50 pixel square) is obtained. A final tally of all identified exosomes along with integrated Raman intensities is outputted to an Excel file for further analysis.

Data Analysis

For each sample, a negative control without primary antibody is measured. To analyze the data, the control is used to establish a cutoff value of the fluorescent signals to be used to identify protein positive exosomes. A false positive rate (FPR) no greater than 0.01 from the control sample is used to set this cutoff value to calculate the fraction of protein-positive exosomes, $F_p$, and the mean expression level of the protein over the examined exosomes, $\zeta_p$.

Figure 12:
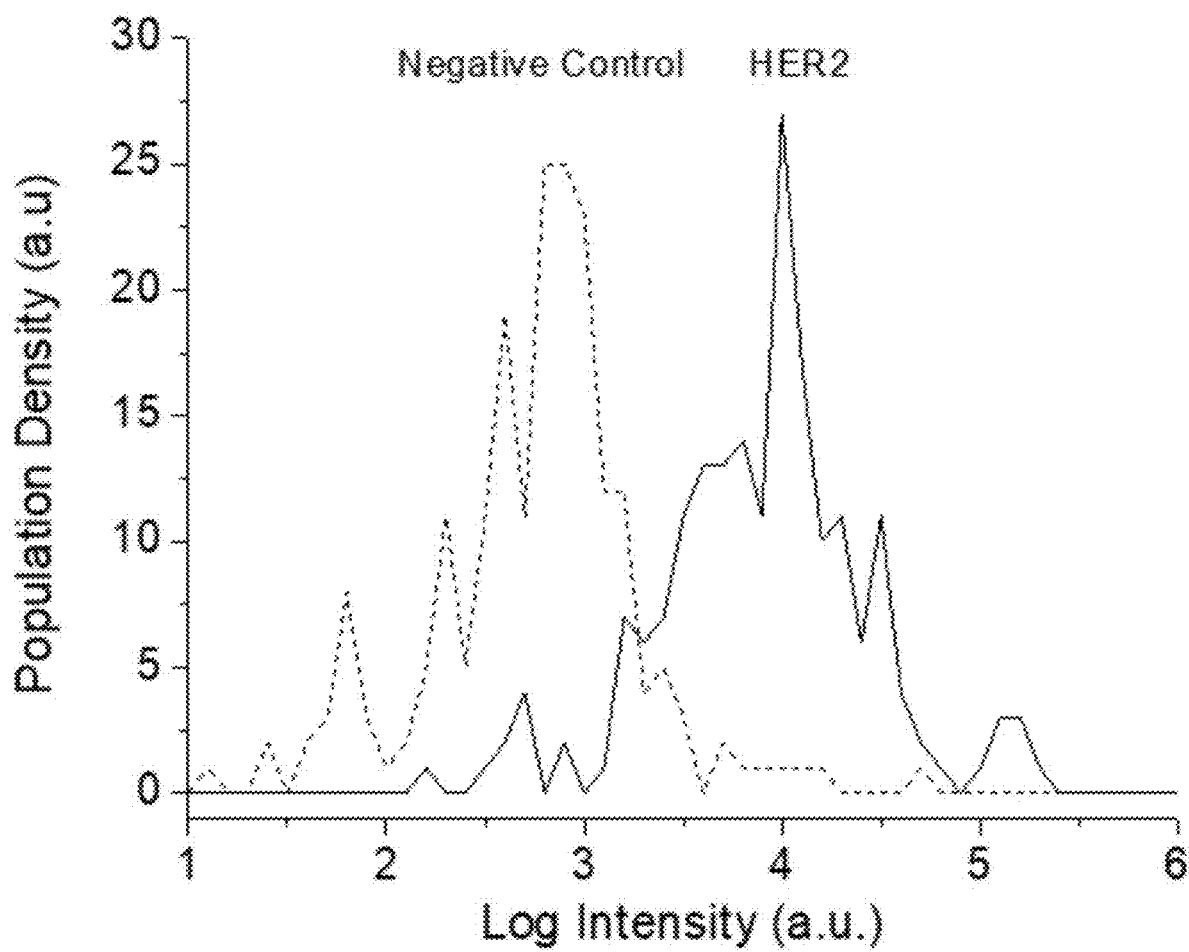
FIG. 12 show an example of protein profiling with the fluorescent nanoparticles using dark field imaging as the mask and Magdye as the fluorescent nanoparticles. In this case, the mask and target images of SKBR3 exosomes detect HER2 cancer protein marker using a commercial confocal microscope.

FIG. 12 shows an example for HER2 profiling on SKBR3 exosomes. In this example, HER2 was labeled with 20-nm Magdye with Cy5 and membrane was labeled with Alexa Fluor 405. The images were taken with a regular confocal microscope. The results show that $F_{HER2}=0.7$ and $\zeta_{HER2}=2 \times 10^4$ a.u.

Diagnosing and Treating Disease

The compositions and methods of the present disclosure may be used to diagnose disease. As described supra, molecules associated with disease can become integrated into or onto an extracellular vesicle. The detection and characterization of such vesicles and their disease-associated molecules can provide information relevant for diagnosing a disease, determining the progression or regression of disease, and treating disease. For example, some cancer cells express particular tumor antigens that are associated with a particular stage of the disease. A tumor antigen is a protein that is overexpressed in certain cancers (e.g., breast cancer) that can be used as marker, in some cancers, for determining patient prognosis. Samples obtained from a subject having or suspected of having breast cancer may be analyzed for the presence or absence of a tumor antigen. Those individuals having extracellular vesicles that are positive for the tumor antigen be diagnosed with cancer. In some cases, a subject having cancer who has tumor antigen-positive extracellular vesicles may have a poorer prognosis that a cancer patient without the tumor antigen-positive extracellular vesicles.

A subject having a disease may undergo periodic testing to determine if the level of a cancer marker is increasing, decreasing, or static. For example, a subject having tumor antigen-positive cancer may surveil the amount of tumor antigen-positive extracellular vesicles present in subsequent samples to quickly determine if there is any alteration in the amount of tumor antigen-positive vesicles. If the amount of tumor antigen-positive vesicles in a sample is greater than that observed in a previous sample, the subject's cancer is likely progressing or not responding effectively to treatment. If the number of tumor antigen-positive extracellular vesicles remains static relative to an earlier sample, the disease may be responding treatment sufficiently to stop disease progression, but perhaps not to a level sufficient for disease regression or remission. Conversely, if the number of tumor antigen-positive extracellular vesicles decreases relative to an earlier sample, the subject's disease may be regressing, and the absence of such vesicles may signify remission.

It is contemplated that the compositions and methods in the present disclosure can be used to identify the disease stage of a subject. For example, some markers associated with early stages of disease may be lost, or expressed at a reduced level, as the disease progresses. Thus, the marker profile of a subject's extracellular vesicles can be compared to a reference profile or profiles and a determination made regarding the particular stage of disease the subject is experiencing.

Kits

The present disclosure contemplates kits comprising a tag primary antibody having an affinity for at least one surface bound molecule or at least one lumenal molecule; and a secondary antibody having an affinity for the primary antibody, wherein the secondary antibody comprises a quantum dot label. In some embodiments, the kit further comprises at least one additional primary antibody. In some embodiments of the kits that comprise more than one primary antibody, the kit also comprises at least one additional secondary antibody, wherein each secondary antibody is labeled with a different quantum dot. In some embodiments of the kit, the kit further comprises an array for detecting extracellular vesicles and directions for its use. In some embodiments, the kit further comprises instructions for printing on a 3D printer an array suitable for interrogating samples for the presence or absence of extracellular vesicles and/or molecules associated said extracellular vesicles. In some aspects, a kit comprises an array for detecting extracellular vesicles and directions for its use. In some embodiments, a kit comprises instructions for printing an array on a 3D printer that is suitable for interrogating samples for the presence or absence of extracellular vesicles and/or molecules associated said extracellular vesicles.

The following examples are put forth to provide those of ordinary skill in the art with a complete disclosure and description of how to make and use the assay, screening, and therapeutic methods of the invention, and are not intended to limit the scope of what the inventors regard as their invention.

Example 1: Array Preparation

To detect the presence of extracellular vesicles (exosomes) in a sample, a multi-well cassette was fabricated.

Standard microscope glass slides (75×25×1 mm) (FIG. 4A) were coated with an optically transparent gold film approximately 20 nm thick using a magnetron sputter system (AJA International, Inc., North Scituate, MA) to facilitate slide surface functionalization. Referring to FIGS. 4B and 4C, raised stabilizers on the long edges of the slide enabled fixation of the gold film to the slide, and pressure grease facilitated sealing. 261 wells (9×29) were added to the gold-coated slide using a Formlabs Form 2 3D printer. Each well on the array was about 1.5 mm in diameter and about 0.5 mm in height. Each well had about 0.9 μL capacity and was separated from its nearest neighbors by about 1.0 mm.

The surfaces of the wells were functionalized with capture molecule by saturating the surface of the slide with 0.1 mM 11-mercaptoundecyl tetra (ethylene glycol) (MU-TEG) for 30 minutes to prevent non-specific interactions. Capture antibodies were first modified to comprise a polyethylene glycol thiol (PEG-SH; molecular weight=5,000 kDa) linker, and this antibody was then bound to the functionalized surface of the sample wells by incubating the wells with the capture molecule (50 μg/ml) for about five hours.

Example 2: Capture of Exosomes Comprising CD81

Array slides were prepared as described in Example 1. Plasma samples from a breast cancer patient were analyzed for the presence of exosomes with a tetraspanin marker (i.e., CD81 primary antibody (approximately 2 μg/ml) (commercially available)) that specifically binds tetraspanin CD81 was added to the array and incubated at room temperature for one hour. DiO dye was used to label exosomes to confirm the success capture of exosomes (50 μM, 30 min). Isotype IgG (commercially available) was used to replace the CD81 capture antibody for a negative control. IgG is a primary antibody that lacks specificity to the target but matches the type and class of the primary antibody used in the cancer marker targeting. IgG was used as the negative control to help differentiate non-specific background signal from specific antibody signal. The assays were then analyzed for fluorescence. FIG. 6A shows the abundant exosomes captured with CD81 antibodies, indicating the presence of exosomes comprising the CD81 marker. Conversely, the IgG control shows very little fluorescence (FIG. 6B), which suggests that exosomes can be specifically captured directly from plasma with antibodies to the tetraspanin markers.

Example 3: Exosome Labeling with Fluorescence Nanoparticles

Exosomes in cell culture media or plasma are diluted over 100× with phosphate buffered saline (PBS) and filtered through a 0.2 μm polyethersulfone (PES) filter to remove debris and larger, non-exosome vesicles. Exosome membranes were then biotinylated with a 50 μM lipophilic cholesterol-PEG-biotin (CLS-PEG-biotin) composition for 30 minutes at room temperature. The PEG moiety conjugated to the cholesterol and biotin moieties has a molecular weight of approximately 2,000 g/mol.

To detect the presence of a particular exosome surface protein, primary antibody (approximately 2 μg/ml) having affinity for the exosome surface marker was added to the sample and incubated for one hour at room temperature. Secondary antibody labeled with 20 nM QD655 or Magdye 665 (Magnetic nanoparticles coated with Cy5) having an affinity for the primary antibody was then added to the sample and incubated for one hour at room temperature. If dark field imaging is used to localize exosomes, the exosomes are ready for imaging acquisition. If fluorescence imaging is used to localize exosomes, the exosomes will be labeled with streptavidin-labeled QD525 (20 nM, 30 min) when QD655 are used for protein detection or streptavidin-Alex Fluor 405 (2 μg/mL, 30 min) when Magdye665 is used for protein detection. The streptavidin binds to the CLS-PEG-biotin labels on the exosome. Labeled exosomes were fixed with 2% paraldehyde for 15 minutes, stored at 4° C., and measured within a week of preparation.

Example 4: Exosome Labeling with Amplified Fluorescence Nanoparticles

Exosomes in cell culture media or plasma are diluted over 100× with phosphate buffered saline (PBS) and filtered through a 0.2 μm polyethersulfone (PES) filter to remove debris and larger, non-exosome vesicles. Exosome membranes were then biotinylated with a 50 μM lipophilic cholesterol-PEG-biotin (CLS-PEG-biotin) composition for 30 minutes at room temperature. The PEG moiety conjugated to the cholesterol and biotin moieties has a molecular weight of approximately 2,000 g/mol.

To detect the presence of a particular exosome surface protein, primary antibody (approximately 2 μg/ml) having affinity for the exosome surface marker was added to the sample and incubated for one hour at room temperature. Secondary antibody conjugated with biotin was then added to the sample and incubated for one hour at room temperature. After washings, 20 nM QD655-streptavidin or Magdye665-streptavidin was then added to the sample and incubated for one hour at room temperature. If dark field imaging is used to localize exosomes, the exosomes are ready for imaging acquisition. If fluorescence imaging is used to localize exosomes, the exosomes will be labeled with streptavidin-labeled QD525 (20 nM, 30 min) when QD655 are used for protein detection or streptavidin-Alex Fluor 405 (2 μg/mL, 30 min) when Magdye665 is used for protein detection. Labeled exosomes were fixed with 2% paraldehyde for 15 minutes, stored at 4° C., and measured within a week of preparation.

Example 5: Two-Color Exosomal Protein Detection with QDs

Figure 7B:
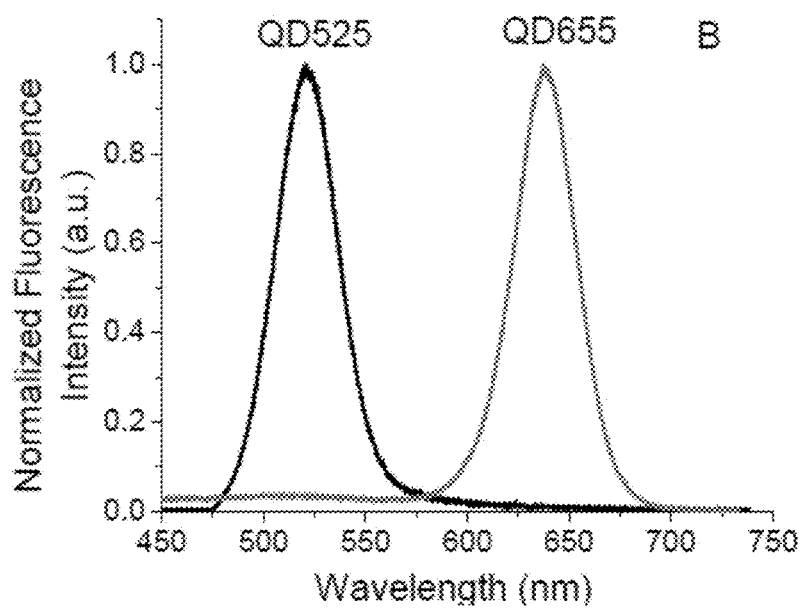

A two-color quantum dot detection method is employed to detect the protein markers of exosomes in a sample. QD525 is used to label the exosome membrane and QD655 is used to label the proteins within the exosome's lumen. These QD labels have overlapping absorption spectra, but distinctive emission spectra. Specifically, QD525 and QD655 are both excitable at 400 nm (FIG. 7A), but have 525 nm and 655 nm maximum emission wavelengths, respectively (FIG. 7B). Emitted fluorescence is correlated to the number of exosomes, and the amount of proteins contained therein, in a sample. This system can thus be used as a quick bulk method for protein profiling.

The two QD probes also provide a quick and reliable method for single vesicle analysis. Signals from both QD525 and QD655 are used to detect and localize individual exosomes. A long pass filter is used to block fluorescence emission from QD525 when measuring signals from proteins of the same exosome. This single vesicle technique is extremely simple and high speed, capable of completing one measurement in seconds.

A versatile optical microscopic system for exosome detection, as shown in FIG. 5 integrates an optical microscope (Nikon, LV 150N) with a pulsed wavelength-tunable laser. Specifically, a modified Nikon LV 150N microscope with bright/dark field modes is used for optical excitation and detection. The sample is mounted on 3D nm resolution translation stages (Newport, model 9063) and is illuminated by a halogen white light source (grey path) for bright/dark field observations. The samples can also be excited by a tunable laser through an objective lens for fluorescence measurements. The Chameleon II laser system (Coherent Inc.) provides excitation wavelengths ranging from about 780 nm to about 1080 nm and the resulting second-harmonic generation from about 340 nm to about 540 nm.

Figure 6B:
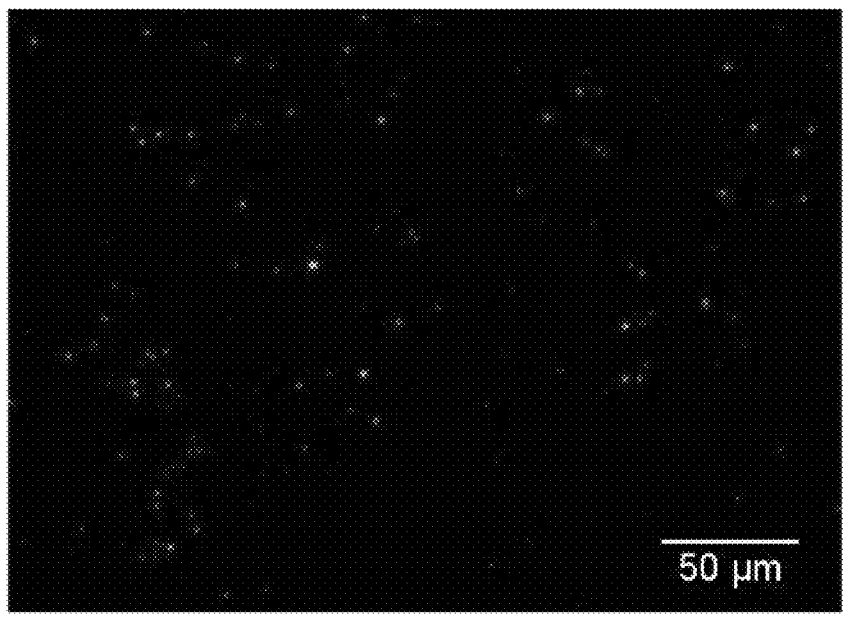

Reflected fluorescent signal from the sample, after passing through the beam splitters, is filtered by an appropriate long-pass filter (to block laser excitation) and refocused onto an intermediate image plane where a small pinhole is used to select single exosomes of interest. An additional filter can be inserted before the intermediate image plane to block use-defined signals for selective detection. The fluorescent signal is either captured by a Photometrics CoolSnap camera for imaging or be analyzed by a spectrometer (Horiba Jobin Yvon, model iHR550) and detected by another charged-coupled-device (CCD) camera (Horiba Jabon Yvon, model Synapse). FIG. 6A shows absorbance as a function of wavelength. FIG. 6B shows fluorescence as a function of wavelength. The spectrometer and CCD are optimized for the visible frequency with up to 95% quantum efficiency that is ideal for single exosome measurements. The described microscope system is fully automated by a set of Labview computer programs that synchronize all optical measurements.

Figure 9C:
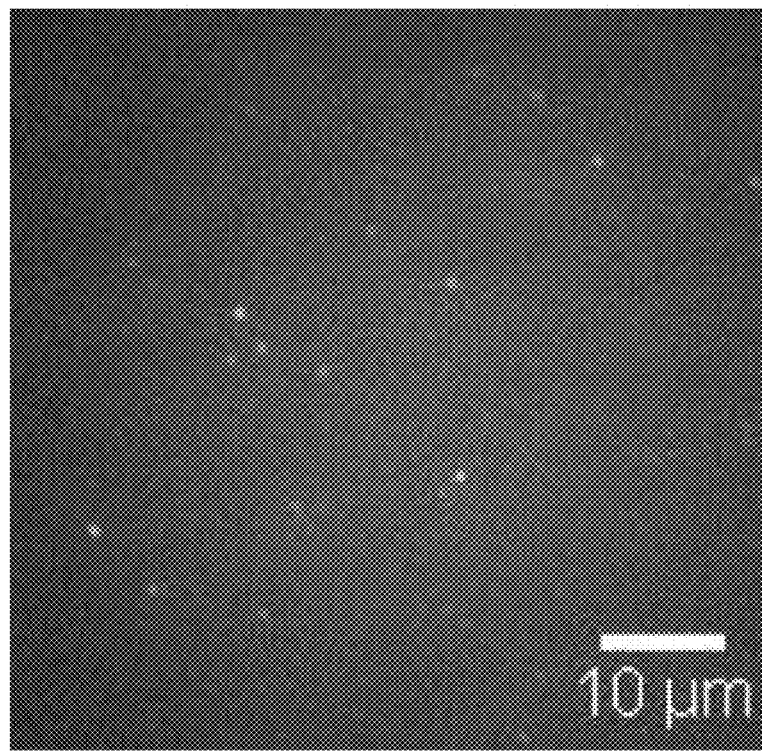

To collect data, exosomes are excited with a 400-nm wavelength (power=1.5 mW). Exosomes are examined under a 100× objective (working distance=1 mm, diameter of field of view: 150 µm) and an image is acquired (one second exposure time) as the mask image (FIG. 9A). Exosomes are visualized using the QD525 signals from the labeled membrane and the QD655 peak from the targeted protein (when the exosomes are positive for protein). Then a spectrum is collected from the exosomes in the image (FIG. 9B), which contains the QD525 peak from the exosome membrane labeling and the QD655 peak from the targeted protein, if the exosomes are positive for the protein. A 600-nm long-pass filter is inserted in front of the imaging camera and an image is acquired (FIG. 9C). This image only collects signals from QD655 as all signals from wavelengths below 600 nm are blocked. The process is repeated for multiple areas in a well for statistical analysis of the vesicle ensemble.

Figure 9D:
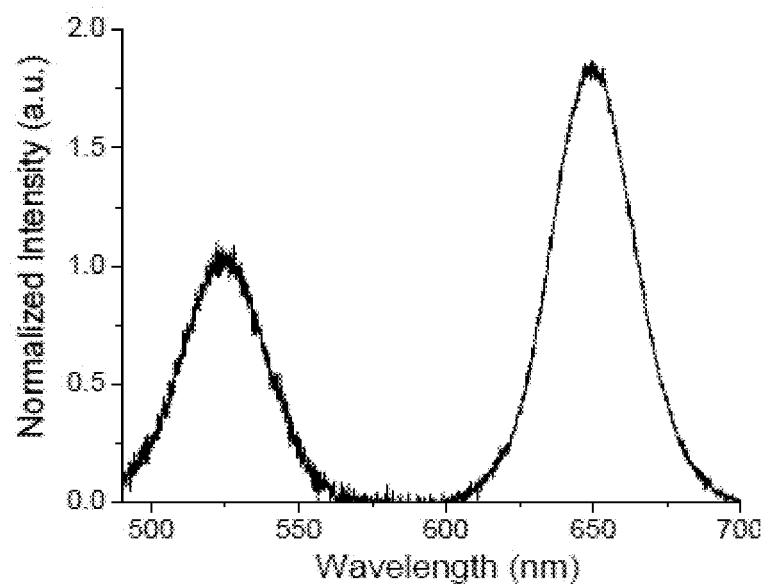

The bulk measurement of a vesicle ensemble is based on the fluorescence spectrum collected from the ensemble. For quantitative analysis, the amount of exosomes under the laser beam was calibrated by normalizing the QD525 peak (FIG. 9D). The value of the detected QD655 signal from the normalized spectrum represents the expression level of the targeted protein from the exosomes under the laser beam. The averaged value from distinct locations of the sample (about 10 spectra) was then used to represent the expression level of the targeted protein. In this example, the protein expression of CD44 from MM231 (mammary gland/breast derived from metastatic site) exosomes was 2.1 a.u.

Example 6: Two-Color Exosomal Protein Detection with Magdyes

A two-color detection method with dye-containing nanoparticles is employed to detect the protein markers of exosomes in a sample. Magdye665 is used to label the exosome membrane and Alex Fluor 405 is used to label the proteins within the exosome's lumen. These dyes have distinctive fluorescence properties (FIG. 8). Specifically, Magdye665 is excited at 639.5 nm and fluorescence is collect at and over 650 nm. Alex Fluor 405 is excited at 407 nm and fluorescence is collected between 440 and 500 nm. Emitted fluorescence from Alex Fluor 407 lightens up exosomes, and emitted fluorescence from Magdye665 informs the observer of the amount of proteins contained in and on an exosome. Images can be collected with a confocal microscope or the single particle system built by the inventors, as described above with QDs.

Figure 10A:
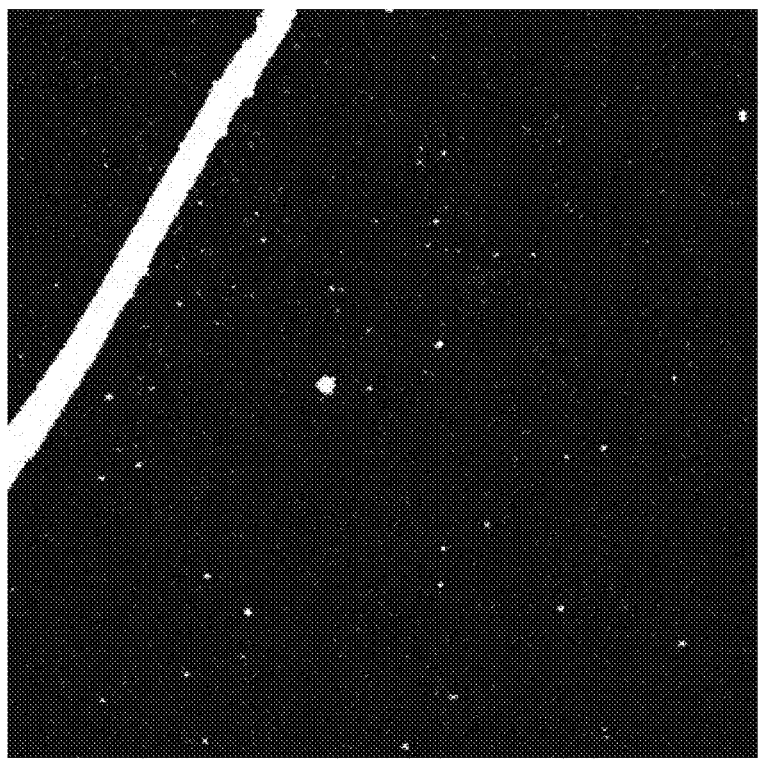
FIGS. 10A-10D are images of collected data summarizing the data collection using Magdyes.
Figure 10B:
Figure 10C:
Figure 10D:
Figure 11A:
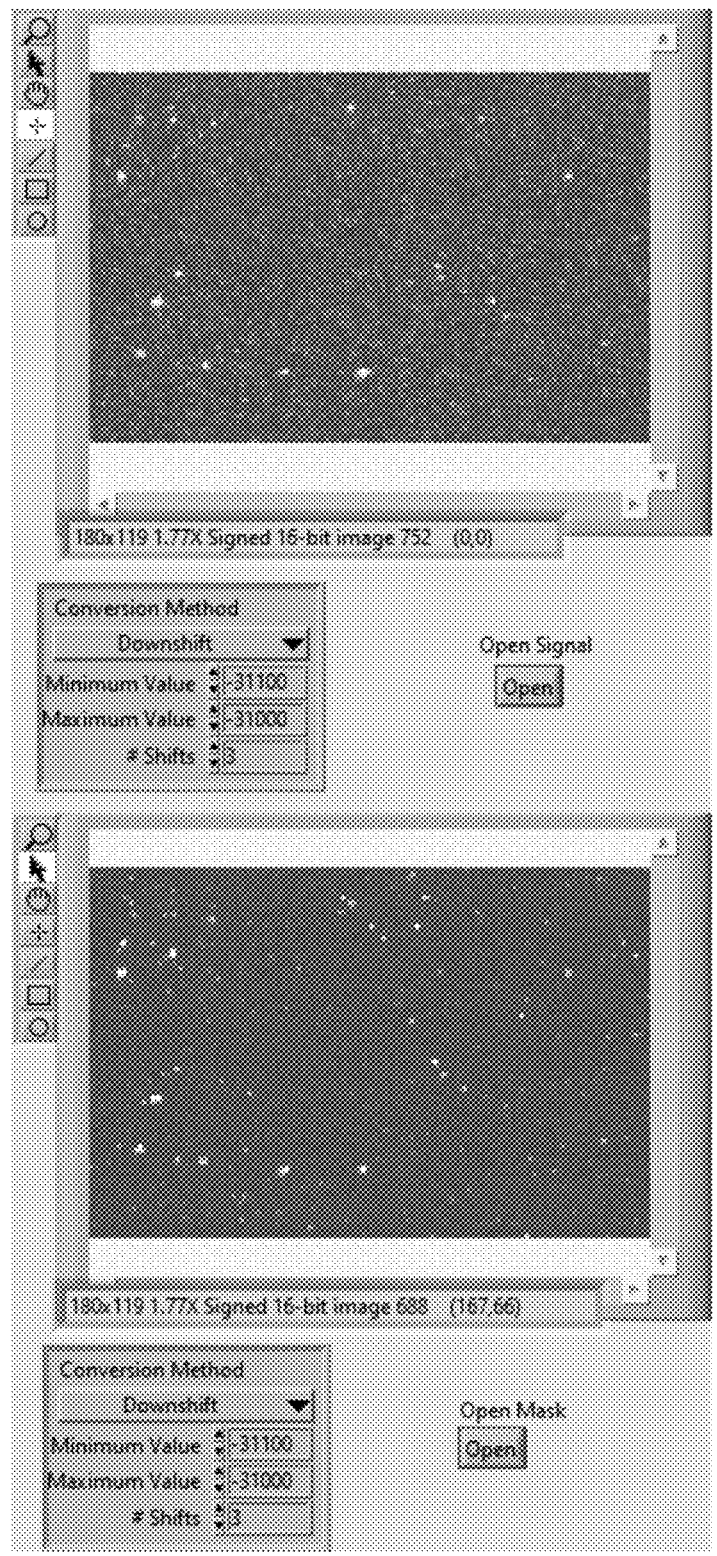
FIGS. 11A-11E show imaging process steps using the Single Exosome Dual Imaging Analysis (SEDIA) software that allows for identification of individual exosome and obtain fluorescence signal intensity from the targeted protein marker integrated over the exosome area.
Figure 11B:
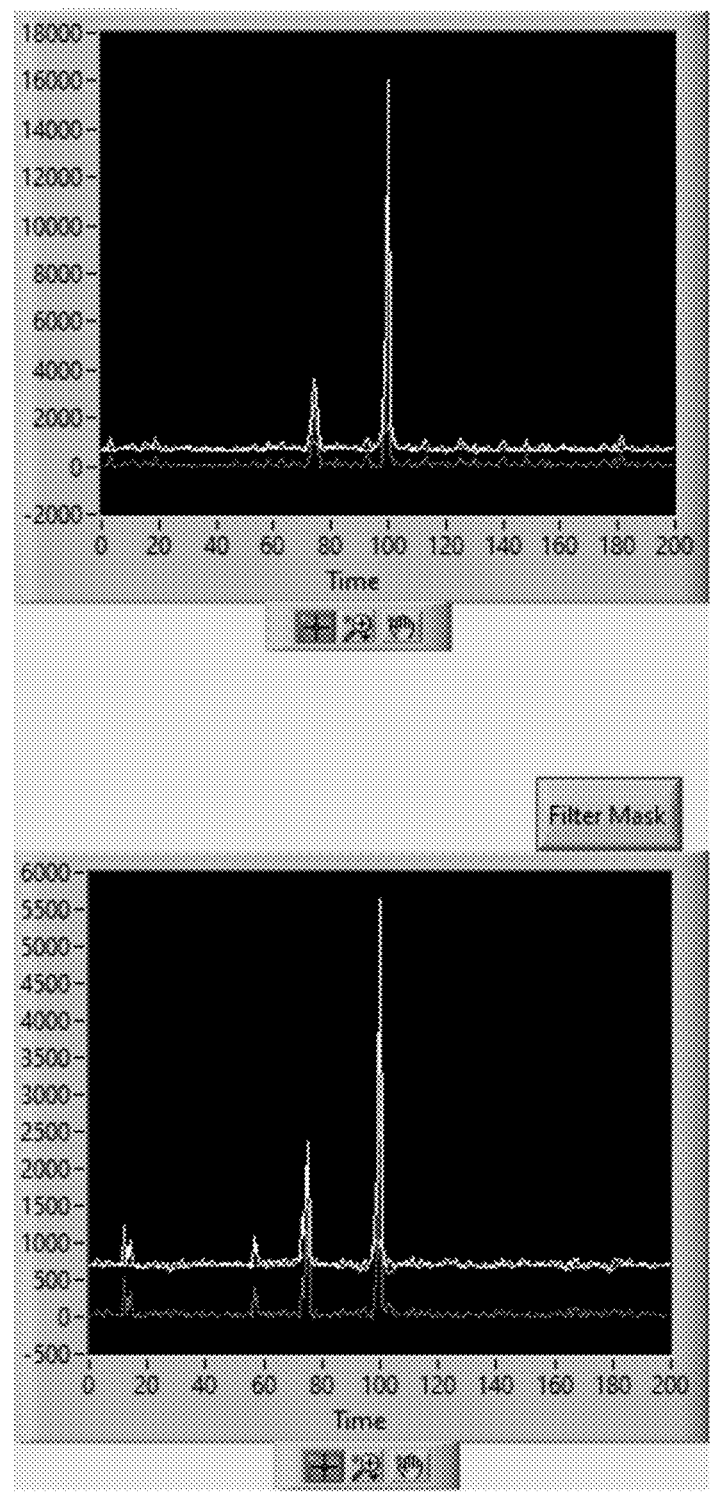
Figure 11C:
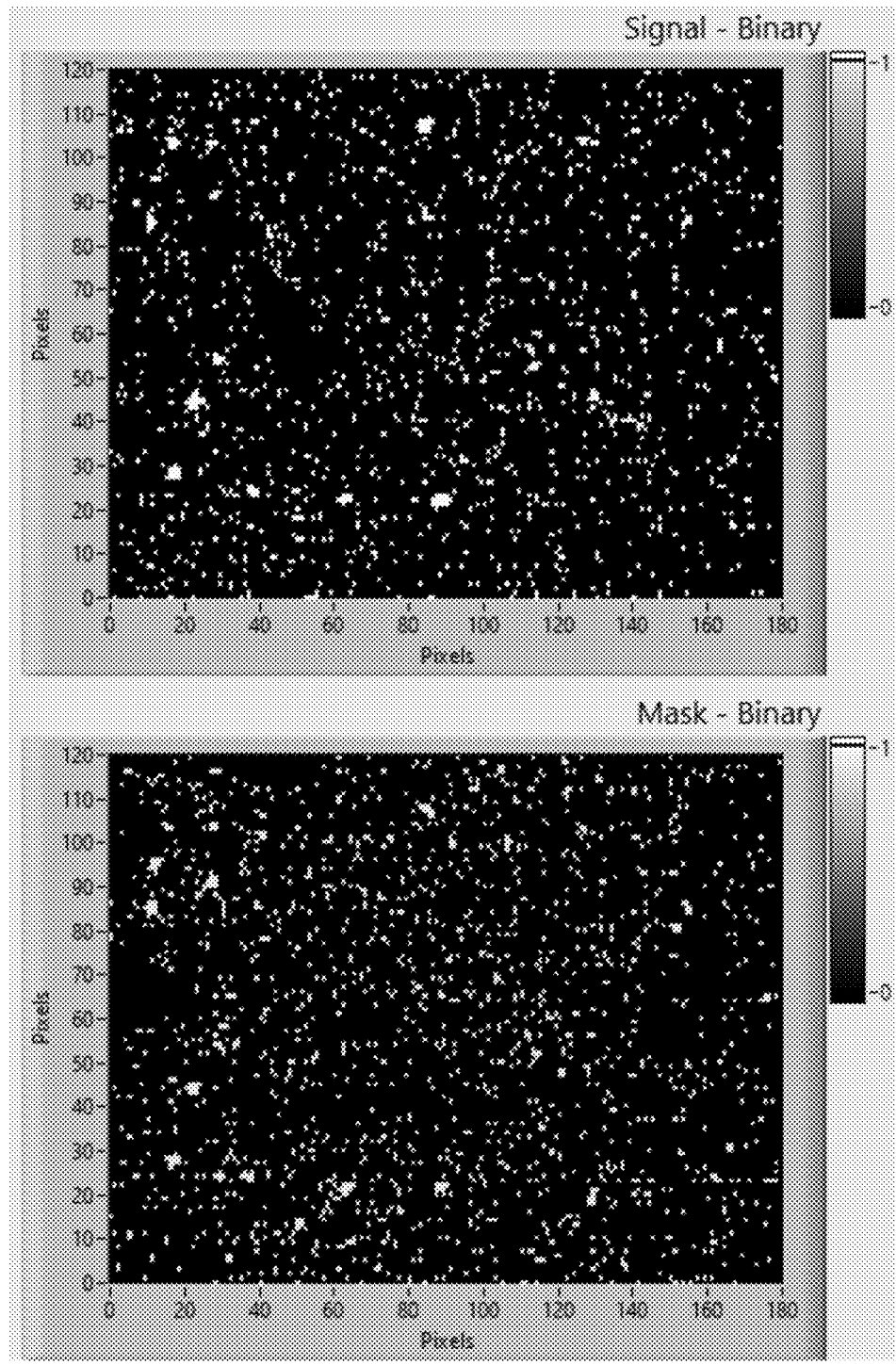
Figure 11D:
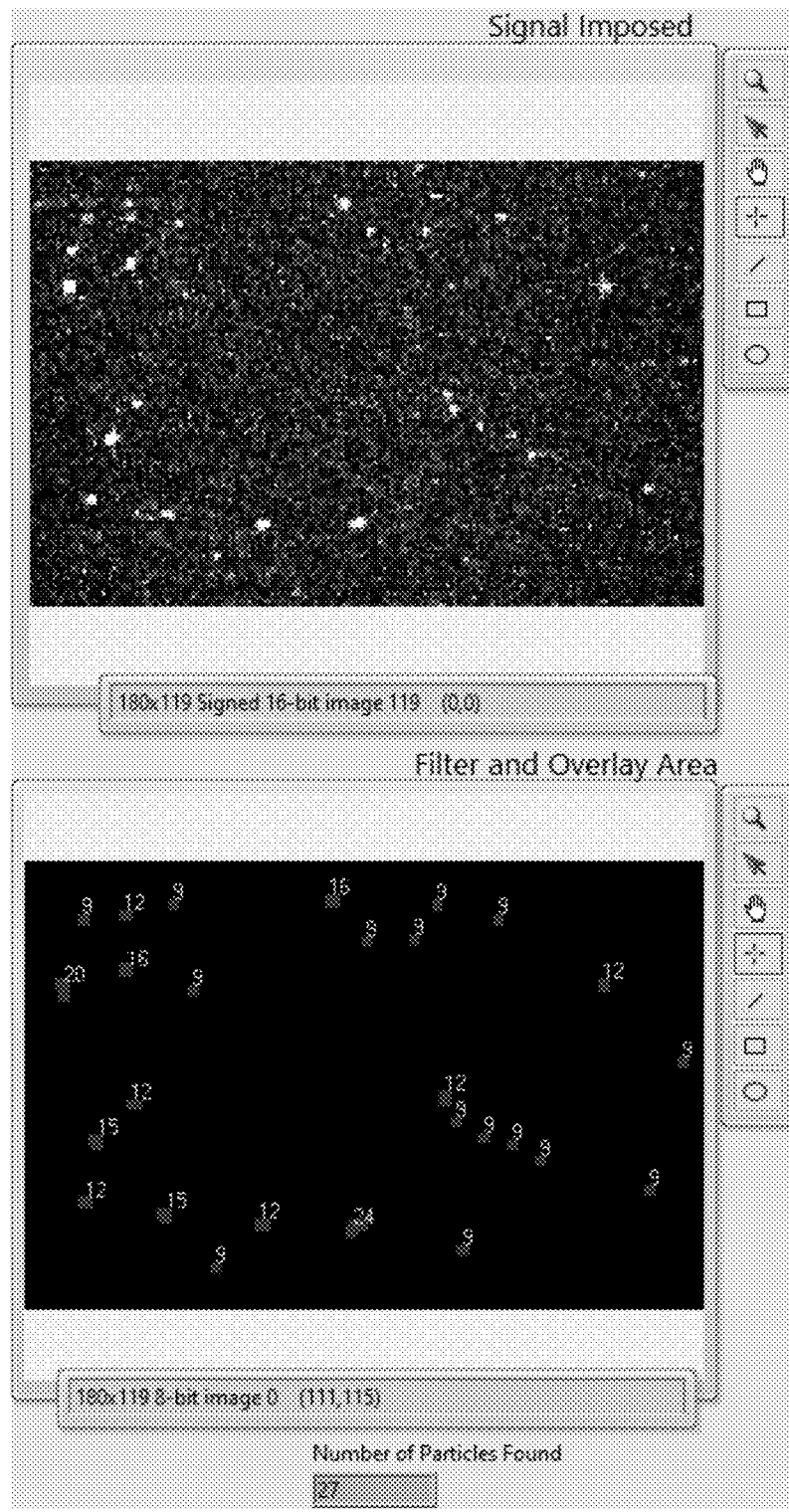
Figure 11E:
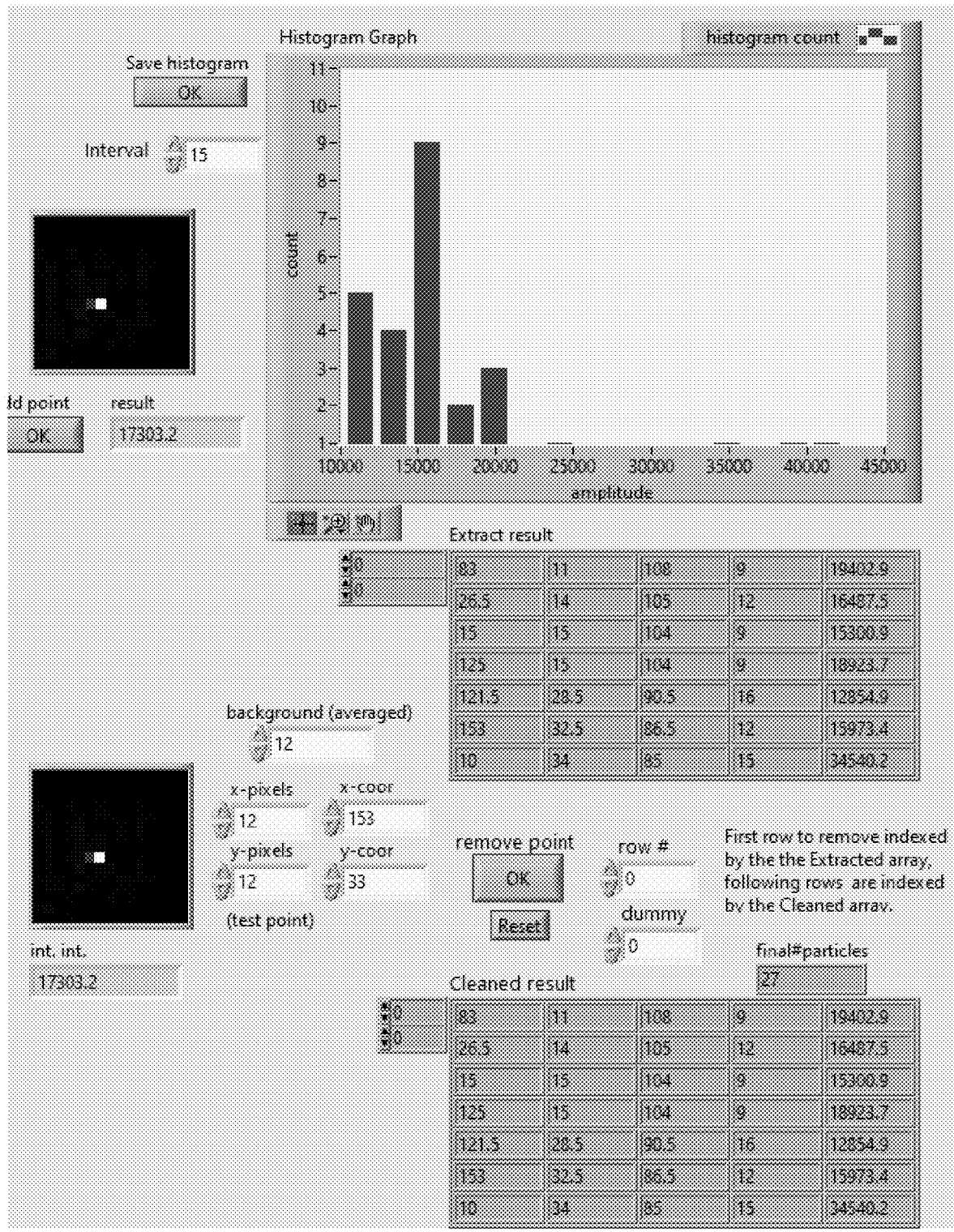

Fluorescence images were acquired using a confocal scanning fluorescence microscope (Nikon Ti-E A1 R inverted system). The optical section thickness is larger than 0.5 µm depending on the size of the pinhole and the numerical aperture (NA) of the objective. Thus, signals from a whole exosome are collected. A 20× objective with NA=0.45 (working distance=4 mm) was used for image acquirement. A DAPI filter (excitation: 407.5/30, emission: 460/60) was used to collect signals from Alexa Fluor 405 and the Cy5 filter (excitation: 639.5/30, emission: 700/75) was used to collect signals from Magdey665. The optimal pinhole size was 153.3 µm for DiB and 233.7 µm for Magdye655. The laser power was low (12 mW) to avoid photobleaching. The images were saved in greyscale for analysis. FIGS. 10A-10D are an example of the target and mask images using SKBR3 exosomes targeting HER2 breast cancer marker. Compared to the negative control (FIG. 10B and FIG. 10C), the HER2 target images show dominate exosomes in the fluorescence image (FIG. 10B). Since not all exosomes express the cancer marker, the mask image (FIG. 10A) shows more exosomes than the target images. FIG. 10D shows the HER2-targeting image labeled with Magdye of the negative control sample.

Example 7: One-Color Detection with QDs

Exosome surface proteins are detected and profiled with QD655 coupled with dark field imaging to localize exosomes. Specifically, QD655 is excited at 407 nm with a confocal microscope or single particle system developed by the inventors. Fluorescence is collect at and over 650 nm. Emitted fluorescence from QD655 inform the amount of proteins contained therein, on an exosome. Dark field imaging of exosomes is collected using the single particle system built by the inventors, as described above with QDs.

Example 8: One-Color Detection with Magdyes

Exosome surface proteins are detected and profiled with Magdye665 coupled with dark field imaging to localize exosomes. Specifically, Magdye665 is excited at 639.5 nm and fluorescence is collect at and over 650 nm. Emitted fluorescence from Magdye665 inform the amount of proteins contained therein, on an exosome. Dark field imaging of exosomes is collected using the single particle system built by the inventors, as described above with QDs.

Example 9: Protein Profiling with Magdyes

Using the two-color exosomal protein detection with Magdyes method described in Example 6, HER2 level on a number of SKBR3 exosomes was characterized (FIG. 12). HER2 is known highly expressed on SKBR3 breast cancer cells. Characterization of HER2 expression on SKBR3 exosomes can validate our approaches. From FIG. 12, it can be seen that SKBR3 exosomes show strong HER2 expression, which is consistent with the parental cell protein expression. Using the negative controls to define the cut-off values, the fraction of HER2-positive exosomes FHER2 was determined to be 0.7. The results show that not all exosomes show high expression of HER2, suggesting the heterogeneity property of exosomes. The mean value of the HER2 expression per exosome 4 was determined to be $2\times10^4$ a.u.

Embodiments of the Disclosure

1. An extracellular vesicle capture and detection system comprising:
    (a) an extracellular vesicle comprising a fluorescent probe, wherein the extracellular vesicle is bound to a capture molecule covalently bound to a film coating the planar support;
    (b) an array comprising a plurality of holes, wherein the array is fixed to the film-coated surface of the planar support to form a plurality of fluid-tight wells;
    (d) a laser tuned to emit a wavelength that can effectively excite the fluorescent probe; and
    (e) a signal collection device for collecting a signal from the excited fluorescent probe.
2. An extracellular vesicle capture and detection system comprising
    (a) an array comprising a plurality of fluid-tight wells, wherein the surface of each well is coated with a film comprising one or more capture molecules covalently bound to the film;
    (b) an extracellular vesicle comprising a fluorescent probespecifically bound to a capture molecule present on the film;
    (c) a laser tuned to emit a wavelength sufficient to excite the fluorescent probe; and
    (d) a signal collection device for collecting a signal from the excited fluorescent probe.
3. The system of claim 1, wherein the planar support is a glass microslide, silicon wafer, or other planar surface.
4. The system of any one of claims 1 to 3, wherein the film is a gold or silver film.
5. The system of any one of claims 1 to 4, wherein the array is plastic, resin, rubber, or silicone.
6. The system of any one of claims 1 to 5, wherein the plurality of fluid-tight wells comprises wells that are about 1 mm in diameter and the inter-well distance is at least about 0.5 mm to about 10 mm.
7. The system of any one of claims 1 to 6, wherein the capture molecule is an antibody, aptamer, or other molecule that specifically binds an antigen present on the surface of an extracellular vesicle.
8. The system of any one of claims 1 to 7, wherein the capture molecule is an antibody that specifically binds ALIX, TSG101, CD81, CD63, or CD9.
9. The system of any one of claims 1 to 6, wherein the capture molecule is a lipophilic composition.
10. The system of claim 9, wherein the lipophilic composition comprises a molecule having an alkyl chain and an affinity for a lipid bilayer of an extracellular vesicle.
11. The system of claim 9 or 10, wherein the lipophilic composition is 1,2-distearoyl-sn-glycerol-3-phosphoethanoloamine conjugated polyethylene glycol thiol (DSPE-PEG-SH).
12. The system of any one of claims 1-11, wherein the fluorescent probe is a fluorescently labeled nanoparticle or a quantum dot.
13. The system of claim 12, wherein the quantum dot is QD525, QD565, QD605, QD655, QD705, or QD800.
14. The system of claim 12, wherein the fluorescently labeled nanoparticle is Magdye665 or Alexa Fluor 405.
15. A method for detectably labeling an extracellular vesicle, the method comprising:
    (a) contacting an extracellular vesicle with a membrane tag comprising a capture molecule; and
    (b) contacting the extracellular vesicle of step (a) with a fluorescent probe under conditions that permit binding of the capture molecule to the fluorescent probe, thereby detectably labeling the extracellular vesicle.
16. The method of claim 15, wherein the fluorescent probe is a fluorescently labeled nanoparticle or a quantum dot.
17. The method of claim 16, wherein the quantum dot is QD525, QD565, QD605, QD655, QD705, or QD800.
18. The system of claim 16, wherein the fluorescently labeled nanoparticle is Magdye665 or Alexa Fluor 405.
19. A method for characterizing an extracellular vesicle, the method comprising:
    (a) contacting the extracellular vesicle with a primary antibody that specifically binds a biomarker present on the extracellular vesicle;
    (b) contacting the extracellular vesicle of step (a) with a secondary antibody that specifically binds the primary antibody, wherein the secondary antibody is conjugated to a first fluorescent probe;
    (c) exposing the extracellular vesicle comprising the fluorescent probe to a wavelength sufficient to elicit a detectable signal from the fluorescent probe; and
    (d) detecting the presence or absence of a signal, thereby characterizing the extracellular vesicle.
20. A method for characterizing an extracellular vesicle, the method comprising:
    (a) contacting the extracellular vesicle with a primary antibody that specifically binds a biomarker present on the extracellular vesicle;
    (b) contacting the extracellular vesicle of step (a) with a secondary antibody that specifically binds the primary antibody, wherein the secondary antibody is conjugated to a first member of a binding pair;
    (c) contacting the extracellular vesicle of step (a) with a streptavidin-conjugated fluorescent probe
    (d) exposing the extracellular vesicle comprising the fluorescent probe to a wavelength sufficient to elicit a detectable signal from the fluorescent probe; and
    (e) detecting the presence or absence of a signal, thereby characterizing the extracellular vesicle.
21. The method of any one of claims 15-20 further comprising capturing the exosome with a capture molecule present on a substrate.
22. The method of claim 21, wherein the substrate is a bead, membrane, wafer, chip, slide, or array.
23. The method of any one of claims 17-22, wherein the wavelength sufficient to elicit a visible signal from the first fluorescent probe is about 400 nm.
24. The method of any one of claims 15-23, wherein the steps of the method are carried out on the system of any one of claims 1 to 14.
25. The method of any one of claims 15-24, wherein the signal detected is proportional to the amount of extracellular vesicles present in the sample.

26. The method of any one of claims 15-25 further comprising:
  incubating the sample with a membrane tag comprising a lipophilic moiety and a biotin moiety, wherein the lipophilic moiety adheres to the lipid membrane of the extracellular vesicle; and
  incubating the sample with a fluorescent probe, wherein the fluorescent probe comprises a streptavidin molecule conjugated to a second fluorescent probe, and wherein the streptavidin molecule binds to the biotin moiety of the membrane tag to effectively label the extracellular vesicle with the fluorescent probe.

27. The method of claim 26, wherein the wavelength sufficient to elicit a visible signal from the first fluorescent probe is sufficient to elicit a signal from the second fluorescent probe.

28. The method of claim 27, wherein the signals emitted from the first and second fluorescent probes are different wavelengths.

29. The method of claim 28, wherein the signal emitted from the second fluorescent probe is proportional to the amount of extracellular vesicles present in the sample.

30. The method of any one of claims 15 to 29, wherein the visible signal emitted from the first fluorescent probe is proportional to the amount of the molecule to be detected in the sample.

31. The method of any one of claims 15-30 further comprising:
  incubating the sample with a second primary antibody that specifically binds a second molecule;
  incubating the sample with a second secondary antibody that specifically binds the second primary antibody, wherein the second secondary antibody is labeled with a third fluorescent probe, and
  exposing the sample to a wavelength sufficient to elicit a visible signal from the third fluorescent probe, wherein the wavelength that effectively elicits a visible signal from the first and second fluorescent probe can effectively elicit a visible signal from the third fluorescent probe that is distinct from the visible signal elicited from the first and second fluorescent probe.

32. The method of claim 31, wherein the visible signal detected from the third fluorescent probe is proportional to the amount of the second molecule in the sample.

33. The method of claim 31 or 32, wherein the signal elicited from the first, second, or third fluorescent probe, or any combination thereof, is collected by a charge-coupled device.

34. The method of claim 33, wherein the signal is from a single exosome.

35. The method of claim 31 or 32, wherein the signal elicited from the first, second, or third fluorescent probe, or any combination thereof, is collected by a spectrometer.

36. The method of claim 35, wherein the signal collected is from more than one exosome.

37. The method of any one of claims 31 to 36, wherein the second molecule or third molecule or both is associated with a disease.

38. The method of claim 37, wherein the amount of the second molecule or third molecule relative to a reference sample is correlated with disease severity or progression.

39. A method of monitoring treatment of a subject having or suspected of having a disease, the method comprising:
  performing the steps of any one of claims 31 to 36 at a time point prior to treatment and at least one time point after treatment commences;
  comparing the initial amount of the second or third molecule to the amount of the second or third molecule after treatment commences; and
  adjusting the treatment protocol if the amount of the second or third molecule is different from the initial amount.

40. A labeled extracellular vesicle comprising a membrane tag having a capture molecule bound to a fluorescent probe.

41. A labeled extracellular vesicle comprising:
  (a) a biomarker present on the extracellular vesicle;
  (b) a primary antibody bound to the biomarker present on the extracellular vesicle;
  (c) a secondary antibody bound to the primary antibody, wherein the secondary antibody is conjugated to a first fluorescent probe.

42. The labeled exosome of claim 40 or 41, wherein the fluorescent probe is a fluorescently labeled nanoparticle or a quantum dot.

43. The labeled exosome of claim 42, wherein the quantum dot is QD525, QD565, QD605, QD655, QD705, or QD800.

44. The system of claim 42, wherein the fluorescently labeled nanoparticle is Magdye665 or Alexa Fluor 405.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An extracellular vesicle capture and detection system comprising:
  (a) an extracellular vesicle derived from a cancer cell, the extracellular vesicle comprising first and second fluorescent dyes, each having emission spectra that are separated and do not interfere with each other, wherein the first fluorescent dye is a mask labelling agent, and comprises a cholesterol-poly(ethylene) glycol lipophilic linker that binds to an exosome membrane to image and localize the exosome using dark field imaging, and the second fluorescent dye is a target labelling agent and comprises specific binding partners that specifically binds a cancer protein marker, wherein the target labelling agent labels the cancer protein marker to detect, image, and quantify the cancer protein marker on the membrane of the extracellular vesicle, and wherein the extracellular vesicle is bound to a capture molecule covalently bound to a film coating a planar support;

(b) an array comprising a plurality of holes, wherein the array is fixed to the film-coated surface of the planar support to form a plurality of fluid-tight wells;

(c) a laser tuned to emit a wavelength that can effectively excite the two fluorescent dyes;

(d) a signal collection device configured for collecting a signal from the excited fluorescent dyes, and converting the signal into mask and target images, where the fluorescent signals from the first fluorescent dye and the second fluorescent dye are at different wavelengths and wherein the detection system comprises a white light source for dark field imaging and the mask image is an image obtained by dark field imaging; and (e) software configured to analyze the mask and target images and convert them into a histogram that characterizes the cancer marker present on the exosome.

2. An extracellular vesicle capture and detection system comprising:

(a) an array comprising a plurality of fluid-tight wells, wherein the surface of each well is coated with a film comprising one or more capture molecules covalently bound to the film;

(b) an extracellular vesicle derived from a cancer cell, the extracellular vesicle comprising first and second fluorescent dyes, each having emission spectra that are separated and do not interfere with each other, wherein the first fluorescent dye is a mask labelling agent, and comprises a cholesterol-poly(ethylene) glycol lipophilic linker that binds to an exosome membrane to image and localize the exosome using dark field imaging and the second fluorescent dye is a target labelling agent and comprises specific binding partners that specifically binds a cancer protein marker, wherein the target labelling agent labels the cancer protein marker to detect, image, and quantify the cancer protein marker on the membrane of the extracellular vesicle, and wherein the extracellular vesicle is bound to a capture molecule covalently bound to a film coating a planar support;

(c) a laser tuned to emit a wavelength sufficient to excite the two fluorescent dyes;

(d) a signal collection device configured for collecting a signal from the excited fluorescent dyes, and converting the signal into mask and target images, where the fluorescent signals from the first fluorescent dye and the second fluorescent dye are at different wavelengths and wherein the mask image is an image obtained by dark field imaging;

(e) a white light source for dark field observations; and (f)) software configured to analyze the mask and target images and convert them into a histogram that characterizes the cancer marker present on the exosome.

3. The system of claim 1, wherein the planar support is a glass microslide, silicon wafer, or other planar surface; wherein the film is a gold or silver film; wherein the array is plastic, resin, rubber, or silicone; and/or wherein the plurality of fluid-tight wells comprises wells that are about 1 mm in diameter and the inter-well distance is at least about 0.5 mm to about 10 mm.

4. The system of claim 1, wherein the capture molecule is an antibody, aptamer, or other molecule that specifically binds an antigen present on the surface of an extracellular vesicle.

5. The system of claim 1, wherein the capture molecule is a lipophilic composition.

6. The system of claim 5, wherein the lipophilic composition comprises a molecule having an alkyl chain and an affinity for a lipid bilayer of an extracellular vesicle.

7. The system of claim 6, wherein the lipophilic composition is 1,2-distearoyl-sn-glycerol-3-phosphoethanoloamine conjugated polyethylene glycol thiol (DSPE-PEG-SH).

8. The system of claim 1, wherein the fluorescent dye comprises a nanoparticle or a quantum dot coated with the dye.

* * * * *